United States Patent [19]

Wallace

[11] Patent Number: 5,494,794

[45] Date of Patent: Feb. 27, 1996

[54] DETECTION OF MITOCHONDRIAL DNA MUTATIONS ASSOCIATED WITH ALZHEIMER'S DISEASE AND PARKINSON'S DISEASE

[75] Inventor: Douglas C. Wallace, Atlanta, Ga.

[73] Assignee: Emory University, Atlanta, Ga.

[21] Appl. No.: 963,723

[22] Filed: Oct. 20, 1992

[51] Int. Cl.$^6$ .............................. C12Q 1/68; C12P 19/34
[52] U.S. Cl. ...................... 435/6; 435/91.2; 435/91.52; 935/77; 935/78
[58] Field of Search ................................ 435/6, 91, 91.2, 435/91.52; 935/77, 78

[56] References Cited

U.S. PATENT DOCUMENTS 4,683,202  7/1987  Mullis ....................................... 435/91

OTHER PUBLICATIONS

Randall, *J. Amer. Med. Assoc.* 266(13), 1739–1740 (1991).
Ikebe et al., *Biochem. Biophys. Res. Comm.* 170(3), 1044–1048 (1990).
Ozawa et al., *Biochem. Biophys. Res. Comm.* 176(2), 938–946 (1991).
Wu & Wallace, *Genomics* 4, 560–569 (1989).
Fu–Hai Lin et al., "Detection of Point Mutations in Codon 331 of Mitochondrial NADH Dehydrogenase Subunit 2 in Alzheimer's Brains," *Biochemical and Biophysical Research Communications* 182:238–246.
Wallace, Douglas C., "Mitochondrial Genetics: A Paradigm for Aging and Degenerative Disease?", *Science* 256:628–632 (1992).
Wallace, Douglas C., "Diseases of the Mitochondrial DNA," *Annu. Rev. Biochem* 1992 61:1175–1212 (1992).

Primary Examiner—Margaret Parr
Assistant Examiner—Kenneth R. Horlick
Attorney, Agent, or Firm—Needle & Rosenberg

[57] ABSTRACT

This invention provides a method of Alzheimer's disease and/or Parkinson's Disease. The method comprises detecting in a sample from a subject the presence of a mutation, for example, in nucleotide position 4,336, 3,397, 3,196 or an insertion between positions 956 and 965, of mitochondrial DNA. The presence of the mutation indicates the presence of or a predisposition to Alzheimer's and Parkinson's disease. Since each mutation increases the likelihood of developing or having Alzheimer's and Parkinson's disease, the detection of more than one of the mutations in an individual can increase the probability of having or developing the disease. The invention also provides a method of determining mutations associated with the presence of or predisposition to Alzheimer's and/or Parkinson's disease. The method comprises:

(a) obtaining a mitochondrial DNA-containing sample from a subject with Alzheimer's and Parkinson's disease;

(b) determining the presence of mutations in the mitochondrial DNA;

(c) comparing the mutations to mutations found in a normal subject; and (d) determining which mutations have a greater rate of occurrence in the subject with Alzheimer's and Parkinson's disease.

12 Claims, 15 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATTCCTCCCC ACACTCAGC                                                                 1 9

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ATTCCTCCCC ACACTCACC                                                                 1 9

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CCCCCTCCCC                                                                           1 0

DETECTION OF MITOCHONDRIAL DNA MUTATIONS ASSOCIATED WITH ALZHEIMER'S DISEASE AND PARKINSON'S DISEASE

This invention was made with government support by National Institutes of Health (NIH) grants NS21328 and HL45572, GM46915-01, NS01336, 1P30AG10130-01, 5U01-AG06790-06, 5P50AG05134, and M01RR-00039. The U.S. Government may have certain rights in this invention.

BACKGROUND OF THE INVENTION

Alzheimer's disease is a progressive neurodegenerative disorder characterized clinically by cognitive decline with onset usually after the age of 60 years. Its major neuropathological features include senile plaques, many with abnormal neurites (neuritic plaques), neurofibrillary tangles within neuronal perikarya, and amyloid angiopathy. Several neurotransmitter systems are perturbed in Alzheimer's disease, with cholinergic deficiency being most prominent and associated with cell loss in the nucleus basalis of Meynert[1].

Substantial clinical, pathological, biochemical, and genetic heterogeneity exists in Alzheimer's disease. Frequently, Alzheimer's disease patients exhibit extrapyramidal signs of Parkinson's disease[2,3] and have coexisting neuropathological features of Parkinson's disease (AD+PD). These can include substantia nigra degeneration and Lewy bodies in the pigmented nuclei and nucleus basalis of about 20–40% of neuropathologically confirmed autopsy brains[4,5]. Cases displaying cortical Lewy bodies have been called "diffuse Lewy body disease"[6–10], and are increasingly recognized with and without concomitant Alzheimer's disease pathology. Thus, the clinical and neuropathological features of Alzheimer's disease and Parkinson's disease overlap extensively, suggesting that they may represent a spectrum of disease with related causal mechanisms.

Our recent investigations have suggested that oxidative phosphorylation (OXPHOS) defects may play a role in the pathogenesis of Alzheimer's disease and Parkinson's disease[11,12]. OXPHOS enzyme assays in Parkinson's disease brains have shown Complex I defects[13–15] as well as systemic OXPHOS defects in platelets[16] and skeletal muscle[17, 18]. Similarly, Alzheimer's disease patients have shown Complex IV defects in platelets[19] and abnormalities in mitochondrial respiration in neocortex[20] and fibroblasts[21]. Treatment of normal human fibroblasts with the OXPHOS uncoupler CCCP (carbonyl cyanide m-chlorophenylhydrazone) results in a 10-fold increase in the proportion of cells reacting with an antibody to paired helical filaments and a 157-fold increase in cells reacting to the Alzheimer's monoclonal antibody-50[22], suggesting a linkage between OXPHOS defects and Alzheimer's disease pathology. Abnormal mitochondria with paracrystalline inclusions, like those frequently encountered in the muscle from patients with mitochondrial DNA deletions and point mutations[23], have been described in the brain of a patient with AD+PD pathology[24] and patients with Alzheimer's disease[25].

OXPHOS is composed of five enzyme complexes assembled from 13 mitochondrial DNA (mtDNA) and approximately 50 nuclear DNA subunits. Complex I (NADH:ubiquinone oxidoreductase) contains seven mtDNA coded subunits (ND1,2,3,4,4L,5,6); Complex III (ubiquinol-:cytochrome c oxidoreductase) has one mtDNA coded subunit (cytochrome b); Complex IV (cytochrome c oxidase) has three mtDNA coded subunits (COI, COII, COIII); and Complex V (ATP synthase) has two mtDNA coded polypeptides (subunits 6 and 8). The mtDNA also codes for a complete set of tRNAs and the 12S and 16S rRNAs necessary for mitochondrial protein synthesis[11,12,23].

The cytoplasmic location, high copy number, and elevated mutation rate of the mtDNA result in a unique mitochondrial genetics[11,12,23]. The mtDNA is maternally inherited[26,27], and intracellular mixtures of mutant and normal mtDNAs (heteroplasmy) segregate during mitotic and meiotic replication[28–31]. Different tissues and organs rely on mitochondrial OXPHOS to different extents. Therefore, as OXPHOS declines because of increasingly severe mtDNA mutations, organ specific energetic thresholds are traversed, yielding variable clinical phenotypes[31,32,33]. OXPHOS enzyme activities decline with age[34–36], concomitantly with the age-related accumulation of mtDNA damage in stable tissues[37–40]. This may accentuate inherited OXPHOS defects as individuals age, leading to clinical manifestations late in life[11,12].

As a result of the quantitative aspects of mtDNA genetics, families harboring deleterious mtDNA mutations frequently show highly variable phenotypic expression among maternal relatives[11,12]. This is seen for both heteroplasmic mtDNA mutations which segregate between generations[31, 33] and homoplasmic mutations[41–43], whose expression can be influenced by additional mtDNA mutations[42,44–46], nuclear DNA alleles[47], and/or environmental factors. OXPHOS diseases are further complicated by the fact that different mtDNA mutations can act alone or in synergistic groups to produce the same phenotype[42]. This is best exhibited in Leber's hereditary optic neuropathy (LHON), where the same disease has been associated with mutations in the Complex I ND1, ND2, ND4, and ND5 genes[41,42,44, 45,48–50], in the Complex III cytochrome b gene[42,46], and in the Complex IV COI gene[51].

MtDNA mutations which cause LHON fall into two categories: (1) nucleotide substitutions with low pathogenicity that exist as rare polymorphisms in the general population and increase the probability of expressing the disease phenotype[42,44–46] and (2) nucleotide substitutions with high pathogenicity that cause maternally transmitted disease[41,48–50]. The low pathogenicity mutations typically cause sporadic disease within families and can be identified through phylogenetic analysis by the clustering of patients around specific mtDNA haplotypes[42,44,51]. Within these pathological mtDNA lineages, sequential mutations frequently accumulate, increasing the probability of clinical manifestations[42,44]. The highly pathogenic mutations frequently cause familial disease and occur randomly in the population in association with a variety of mtDNA haplotypes[52].

Moreover, because of the continued importance of Alzheimer's disease and Parkinson's disease, there is an urgent need to diagnose as well as predict a predisposition to the diseases. This invention satisfies this need by demonstrating that defects in mtDNA are associated with Alzheimer's disease and Parkinson's disease and can be used to predict the likelihood of developing Alzheimer's disease and Parkinson's disease and used to diagnose Alzheimer's disease and Parkinson's disease.

SUMMARY OF THE INVENTION

This invention provides a method of diagnosing or predicting a predisposition to Alzheimer's disease and/or Parkinson's disease. The method comprises detecting in a sample from a subject the presence of a mutation, for example, in nucleotide position 4,336, 3,397, 3,196 or an insertion between positions 956 and 965, of mtDNA. The presence of the mutation indicates the presence of or a predisposition to disease. Since each mutation increases the likelihood of developing or having Alzheimer's disease, the detection of more than one of the mutations in an individual can increase the probability of having or developing the disease.

The invention also provides a method of determining mutations associated with the presence of or predisposition to Alzheimer's disease and/or Parkinson's disease. The method comprises:

(a) obtaining a mtDNA-containing sample from a subject with Alzheimer's disease;

(b) determining the presence of mutations in the mtDNA;

(c) comparing the mutations to mutations found in a normal subject; and (d) determining which mutations have a greater rate of occurrence in the subject with Alzheimer's disease.

Figure 1A:
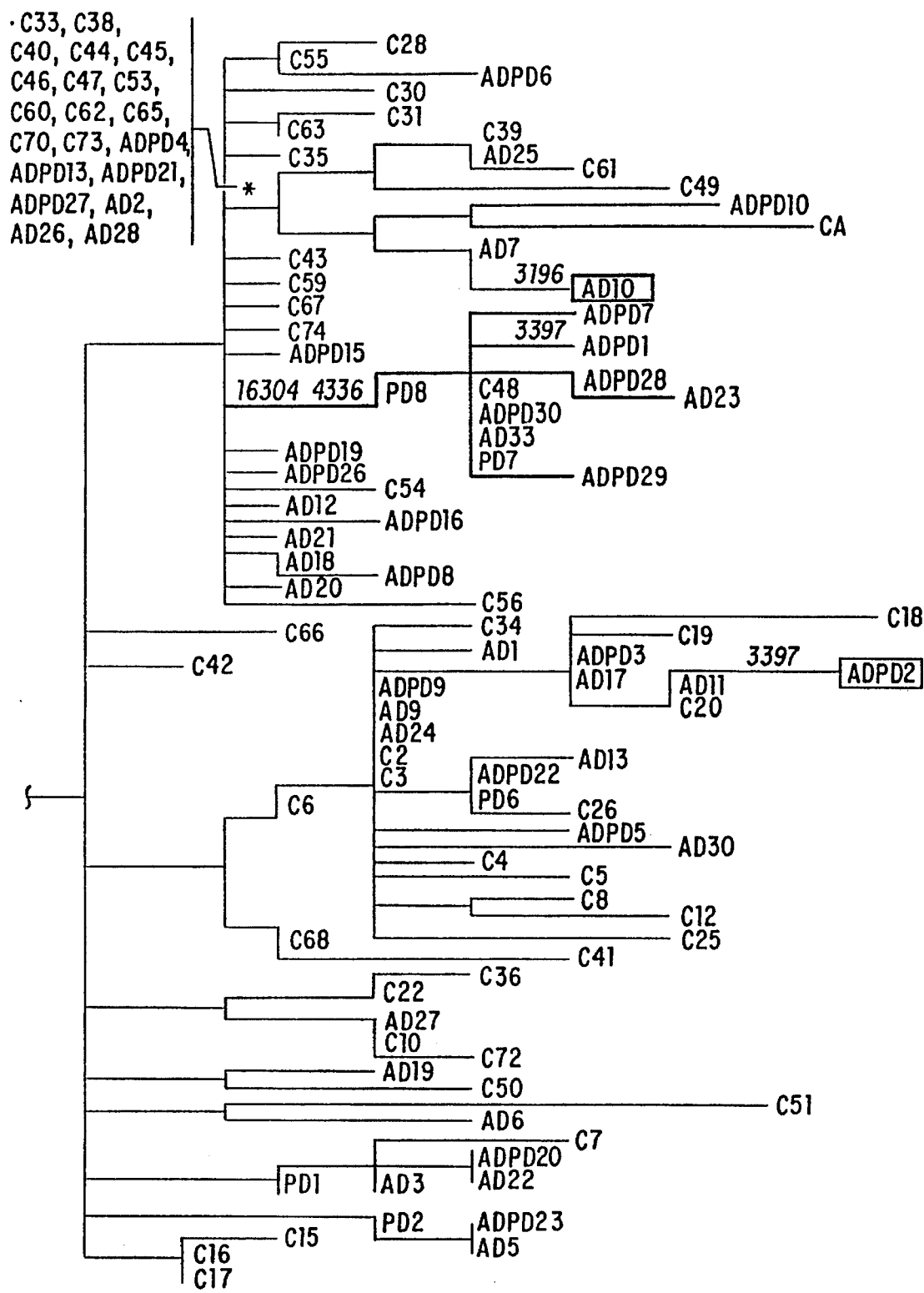
FIG. 1 shows a phylogenetic tree generated by parsimony analysis showing the evolutionary relationship between 71 AD, AD+PD, and PD cases, 74 Caucasian controls, and the Cambridge (CA) sequence[57]. This tree is 164 mutational steps in length with a consistency index of 0.756 and represents one of 100 very similar trees of the same length generated by the Tree-Bisection-Reconnection (TBR) branch swapping method of PAUP. The horizontal branch lengths are proportional to the number of mutational events which separate haplotypes. Italicized numbers on top of branches indicate nucleotide positions of mutations discussed in the text. The mtDNA[16,303-4,336] lineage is highlighted by bold lines. Two additional patients, AD10 and ADPD2, who are outside this lineage but discussed in the text, are designated by boxes.

Polymorphic sites found in all individuals are indicated below by nucleotide position, diagnostic restriction enzyme, and individual code number. Sites are numbered from the first nucleotide of the recognition sequence. A plus (+) indicates a site gain and a minus (−) indicates a site loss relative to the published sequence[57]. Diagonal lines separating restriction sites indicate that a single mutation alters the recognition sequence of more than one enzyme. These sites were considered to be a single site polymorphism in the statistical and phylogenetic analyses. All samples analyzed differ from the published sequence for the following restriction sites: 13702− [HaeIII], 14199− [HincII], and 14268+ [HinfI]. The complete haplotype data set is as follows: 64+ [DdeI] C12; 255+ [HhaI] C21, AD12; 259+ [AluI] C4; 717+ [HinfI] ADPD7; 951− [MboI] AD7, AD10; 956 to 965 [5 bp insertion] ADPD29; 1004− [HincII] ADPD5; 1715− [DdeI] C11, C22, C23, C29, C36, C51, C71, ADPD12, ADPD17, ADPD24, AD29; 1718+ [AluI] C18−C20, ADPD2, ADPD3, AD11, AD17; 1923− [DdeI] C43; 1941+ [HhaI] C49; 2293+ [AluI] AD6; 3192− [DdeI] AD10; 3391+ [HaeIII] AD16, AD32; 3397+ [RsaI] ADPD1, ADPD2; 3759+ [HincII] C51; 4026− [MboI] C56; 4310− [AluI] ADPD8; 4332+ [AluI] C48, ADPD1, ADPD7, ADPD28, ADPD30, AD23, AD33, PD7, PD8; 4360− [HinfI] C41; 4464− [RsaI] ADPD16; 4529− [HaeII] C11, C23, C29, C49, C71, ADPD12, ADPD17, ADPD24, AD29; 4643+ [RsaI] C7, ADPD20, AD3, AD22, PD1; 4685− [AluI] AD20; 4732/35+ [RsaI] C20, ADPD2, AD11; 4745+ [RsaI] ADPD10; 4769− [AluI] all except AD7, AD10; 4793+ [HaeIII] C28, C55, ADPD6; 5003− [DdeI] C25; 5198+ [HinfI] C1, C57; 5261− [HaeIII] C42, ADPD5; 5584− [AluI] C11, C56; 5823− [AluI] C15−C17, C25, C56; 6260− [HaeIII] C21, AD13; 6296− [DdeI] ADPD6, ADPD19; 6377− [DdeI] AD30; 7025+ [AluI] C1−C27, C29, C32, C34, C36, C37, C41, C42, C50−C52, C57, C58, C64, C66, C68, C69 , C71, C72, ADPD2, ADPD3, ADPD5, ADPD9, ADPD11, ADPD12, ADPD14, ADPD17, ADPD18, ADPD20, ADPD22−ADPD25, AD1, AD3−AD6, AD8, AD9, AD11, AD13−AD17 , AD19, AD22, AD24, AD27, AD29−AD32, PD1−PD6; 7055− [AluI] AD30; 7474 − [AluI] C27, C32; 7570+ [MboI] C36; 7697/7702+ [RsaI] C7, ADPD20, AD3, AD22; 8012− [RsaI] C52; 8165+ [HaeIII] C51; 8249+ [AvaII]/8250− [HaeIII] C11, C23, C29, C41, C51, C68, C71, ADPD12, ADPD17, ADPD24, AD29; 8391+ [AvaII]/8391− [HaeIII] C22, C36; 8515− [Dde] ADPD24; 8616− [MboI] C29, C52, C71, ADPD12, AD29; 8678+ [AluI] ADPD23, AD5; 8858+ [HhaI] all except C8, C12; 8894− [HaeIII] C6, C41, C68; 9025− [HaeIII] ADPD16; 9052− [HaeII]/9053− [HhaI] C9, C12, C21, C24, C58, C69, ADPD23 , ADPD25, AD5, AD8, AD15, AD23, AD31, PD2−PD5; 9147+ [DdeI] C19; 9253+ [HaeIII] C49; 9266− [HaeIII] AD6; 9299+ [AluI] C67; 9380− [HhaI] C39, C49, C61, AD25; 9714+ [HaeIII] ADPD23, AD5, PD2; 9984+ [HinfI] C50, AD19; 10028+ [AluI] C11, C23, C29, C71, ADPD12, ADPD17, ADPD24, AD29; 10084+ [TaqI] ADPD18; 10097+ [HaeIII] C41; 10394+ [DdeI] C1, C9, C11, C13, C14, C21, C23, C24, C27, C29, C32, C37, C52, C57, C58, C64, C69, C71 , ADPD11, ADPD12, ADPD14, ADPD17, ADPD18, ADPD24, ADPD25, AD4, AD8, AD14−AD16, AD29, AD31, AD32, PD3−PD5; 10407+ [RsaI] C41; 10598− [AluI] C18, C57; 10631− [DdeI] C54; 10934+ [MboI] C61; 10971− [HinfI] C50; 11001+ [HaeII] /11002+ [HhaI] ADPD18; 11313+ [AluI] C1, AD3, PD1; 11362− [AluI] C51; 11425+ [AluI] C54; 11439+ [MboI] C72; 11469+ [AluI] ADPD25, AD5, PD3; 12345+ [RsaI] C31, C50; 12560− [AluI] C18, ADPD11; 12763+ [AluI] C15; 12810+ [RsaI] C66; 12946+ [DdeI]/12949+ [HaeII]/12950+ [HhaI] C7; 13018+ [HaeIII] ADPD8, AD18; 13325− [RsaI] C5, C7; 13366+ [BamHI]/13367− [AvaII]/13367+ [MboI] C8, C10, C72, ADPD2, AD27; 13404− [TaqI] C59; 13635+ [TaqI] C18, C19, C20, ADPD2, ADPD3, AD11, AD17; 13957− [HaeIII] C18, ADPD6; 14139+ [MspI] AD6; 14304− [AluI] ADPD23, AD5, PD2; 14347+ [RsaI] C25; 14368− [HinfI] all except ADPD10; 14858− [HaeII]/14859− [HhaI] C30; 14869− [MboI] ADPD10, AD21; 14899+ [AluI] ADPD15; 15346+ [RsaI] C26; 15434+ [DdeI] C35; 15606+ [AluI] C10, C30, C72, AD27; 15754+ [DdeI] C11, ADPD17, AD1; 15812− [RsaI] C32; 15861+ [TaqI] C28; 15872+ [RsaI] C50; 15883− [HaeIII] ADPD26; 15894/97+ [RsaI] PD5; 15907+ [RsaI] AD19; 15925− [MspI] C10, C22, C36, C72, AD27; 16049− [RsaI] AD19; 16065− [HinfI] C27, C32, C37, C57, C64, ADPD11, ADPD14, AD4, AD14, AD16, AD32; 16145+ [HaeIII] AD30; 16180+ [MboI] C51; 16208− [RsaI] C31, C63; 16216+ [HincII] C66; 16238+ [TaqI] C74; 16303− [RsaI] C34, C48, ADPD1, ADPD7, ADPD28, ADPD29, ADPD30, AD23, AD33, PD7, PD8; 16310− [RsaI] AD23, ADPD28; 16389+ [BamHI]/16390+ [MboI]/16390− [AvaII] C11, C18, C23, C29, C71, ADPD12, ADPD17, ADPD24, AD29; 16389+ [HinfI]/16390− [AvaII] C51, AD6; 16398+ [HaeIII] C26, PD6, ADPD22, AD13; 16436+ [RsaI] C5; 16467/78+ [DdeI] C39, C61, AD25; 16494+ [MspI] C9; 16517+ [HaeIII] C7, C9−C11, C13−C17, C21−C24, C28, C30− C33, C35, C36, C38, C40−C47, C50−C56, C58−C60, C62, C63, C65−C74, ADPD4, ADPD6, ADPD8, ADPD11–ADPD13, ADPD15–ADPD21, ADPD23–ADPD27, AD2, AD3, AD5, AD6, AD8, AD12, AD15, AD18–AD22, AD26–AD29, AD31, PD1–PD5, PD8.

The haplotype of the Senegalese used as the African outgroup was 907+ [TaqI], 2390+ [MboI], 2758– [RsaI], 3592+ [HpaI], 4769– [AluI], 7025+ [AluI], 7055– [AluI], 8858+ [HhaI], 10394+ [DdeI], 10806+ [HinfI], 13702– [HaeIII], 14199– [HincII], 14268+ [HinfI], 14368– [HinfI], 16517+ [HaeIII].

Figures 2A, 2B:
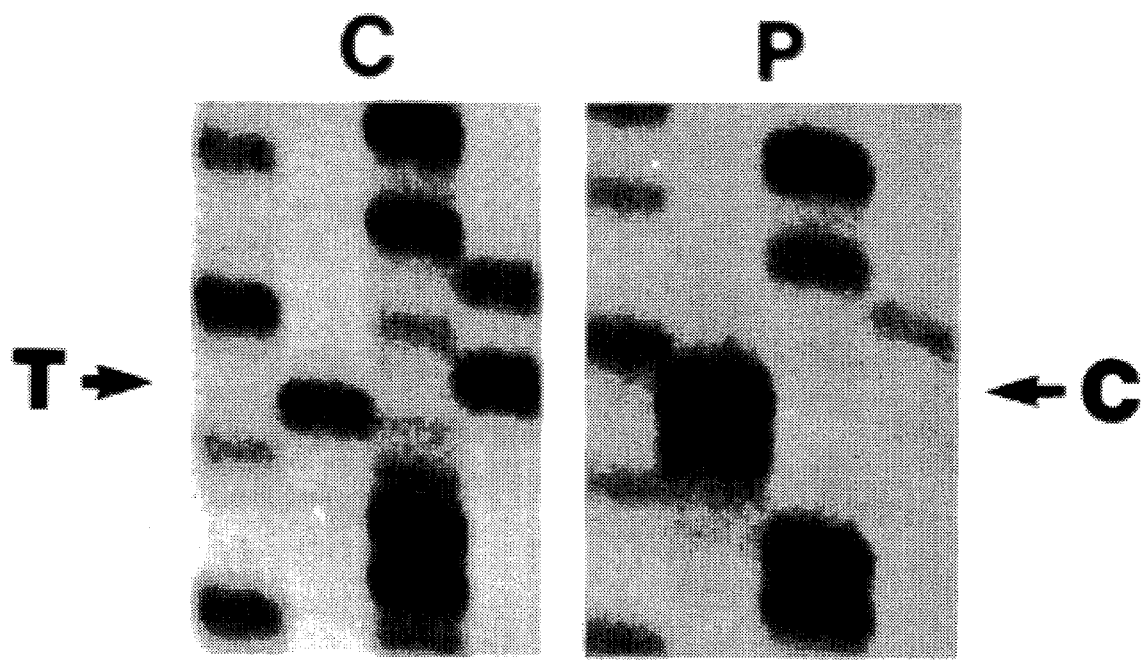

FIG. 2 shows the nucleotide sequence of the np$^{4,336}$ mutation from a control (C) and patient (P). Dideoxy nucleotide sequencing reactions for A, C, G, and T are loaded left to right. The A to G transition was sequenced on the complementary strand and is indicated by arrows as a T to C transition.

Figure 1B:
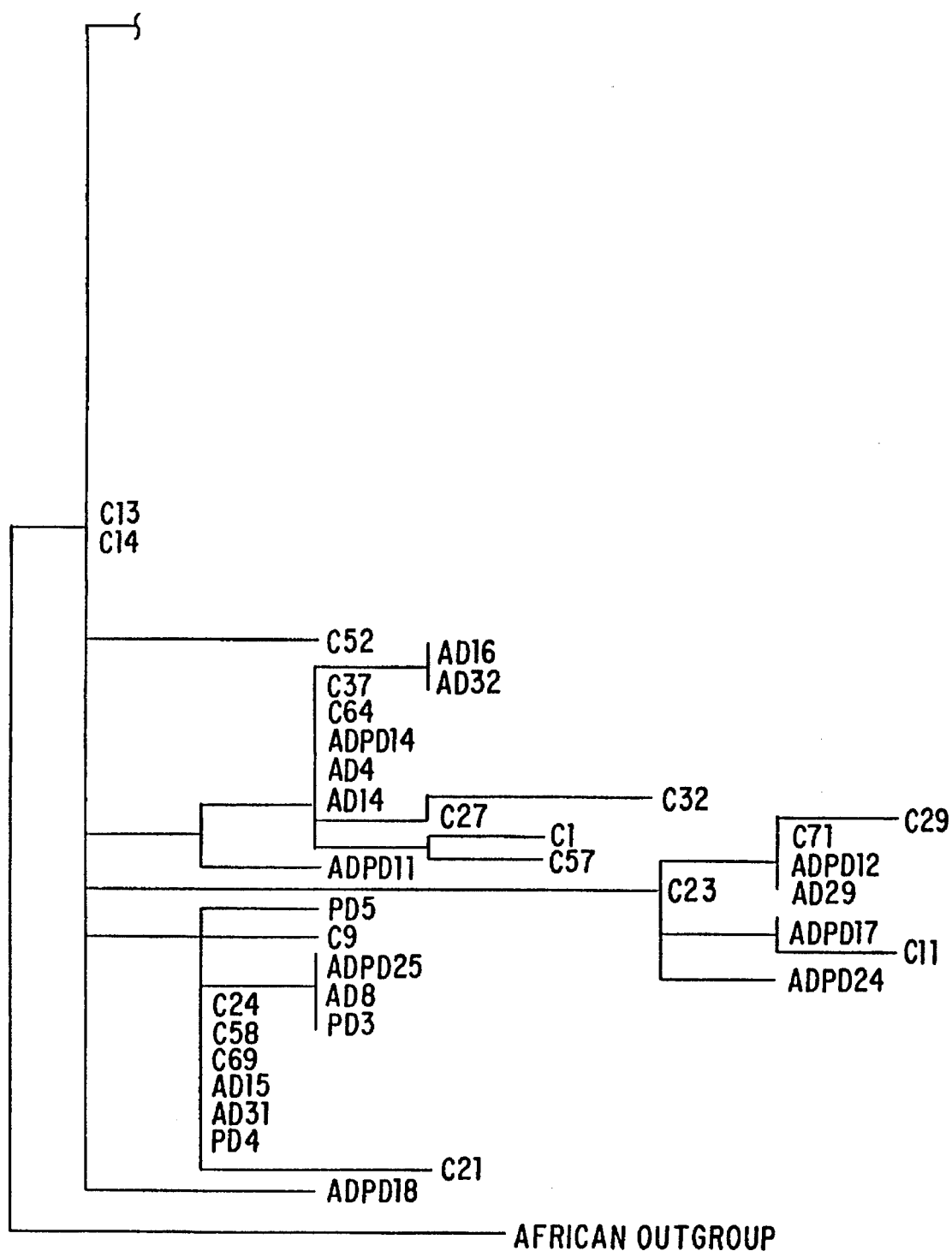
Figure 3:
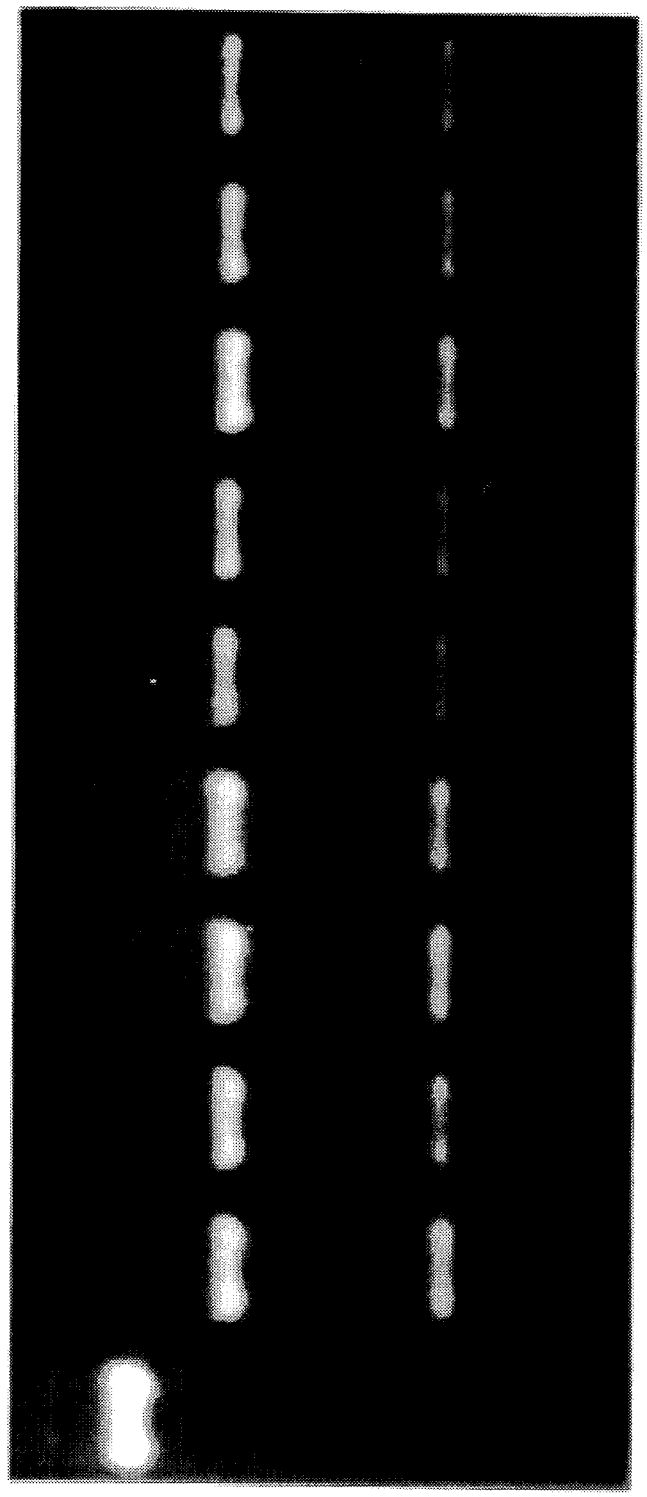

FIG. 3 shows the AvaII digestion of a 1142 np PCR segment encompassing the tRNA$^{Gln4,336}$ mutation. Lane 1 is a control in which the fragment remains undigested. Lanes 2 to 10 are the nine AD, AD+PD, and PD patients identified in the mtDNA$^{16,304-4,336}$ lineage (FIG. 1). The tRNA$^{Gln4,336}$ mutation causes the 1142 np fragment to be cut into 735 and 407 np fragments.

Figure 4:
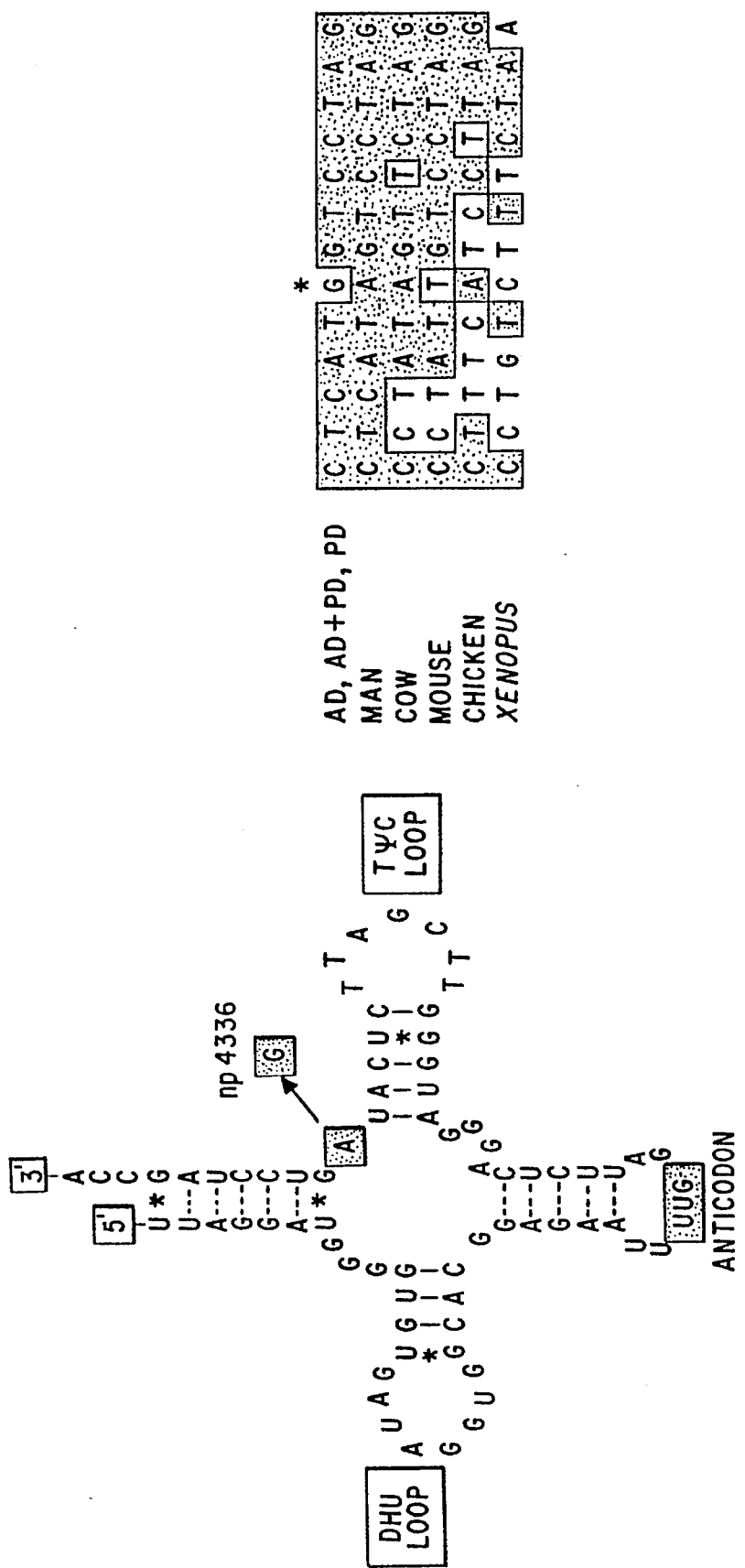

FIG. 4 shows the secondary structure of the tRNA$^{Gln}$ showing the position of the np 4336 point mutation (shaded). Standard base pairing: lines or dashes; non-standard base pairing: asterisks. The homology surrounding the np 4,336 mutation is presented for vertebrates, with the nucleotides corresponding to the np 4,336 mutation indicated by an asterisk. Nucleotides identical with the human sequence are shaded.

Figures 5A, 5B:
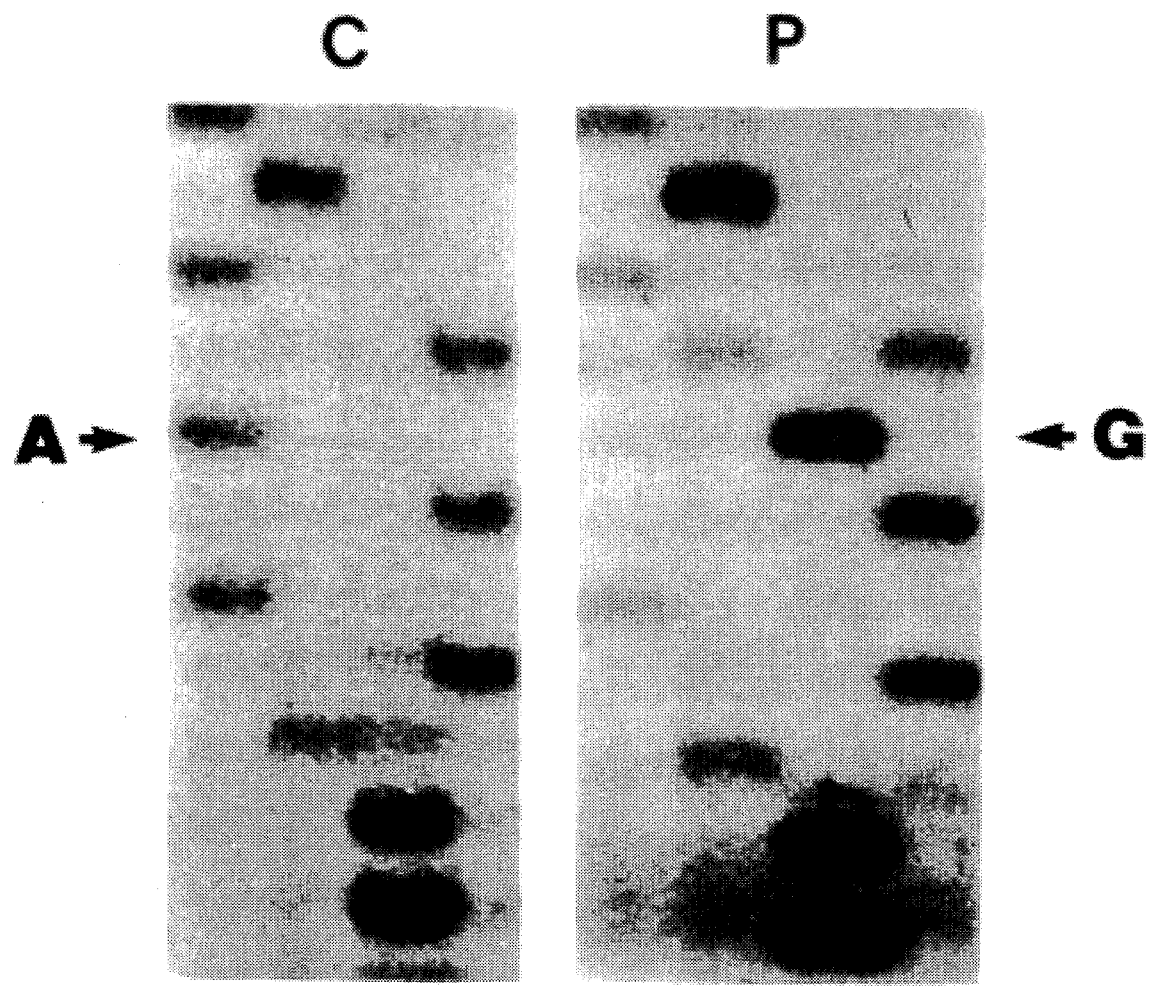

FIG. 5 shows the nucleotide sequence of the np 3,397 mutation from a control (C) and patient ADPD1 (P). Dideoxy nucleotide sequencing reactions for A, C, G, and T are loaded left to right. The A to G transition at np 3397 is indicated by arrows.

Figure 6:
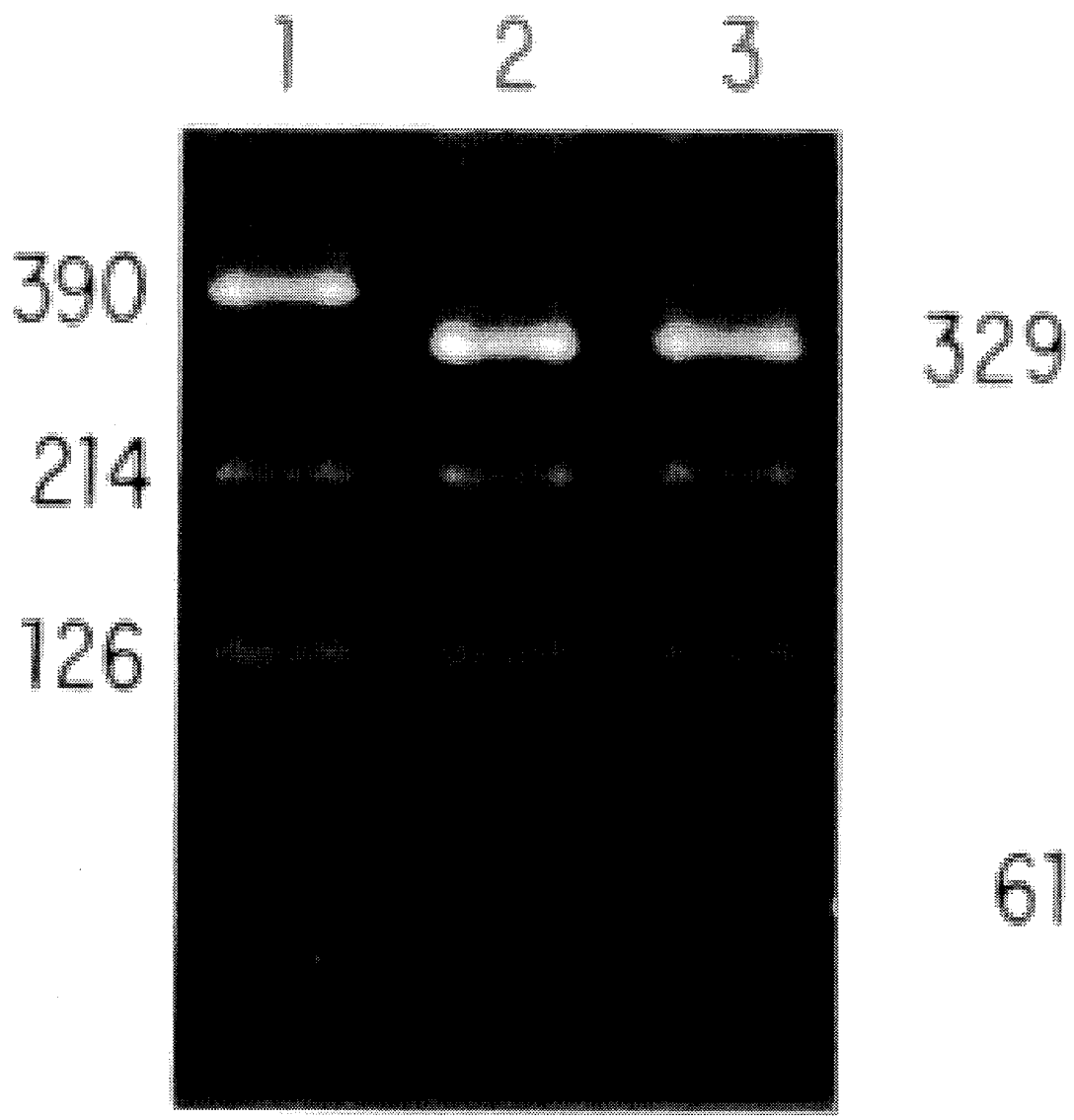

FIG. 6 shows the RsaI digestion of a 730 np PCR fragment encompassing the ND1 np 3,397 mutation. Lane 1 is a control in which the 390 np fragment remains undigested. Lanes 2 and 3 are patients ADPD1 and ADPD2 in which the fragment is cut into 330 and 60 np fragments.

Figure 7:
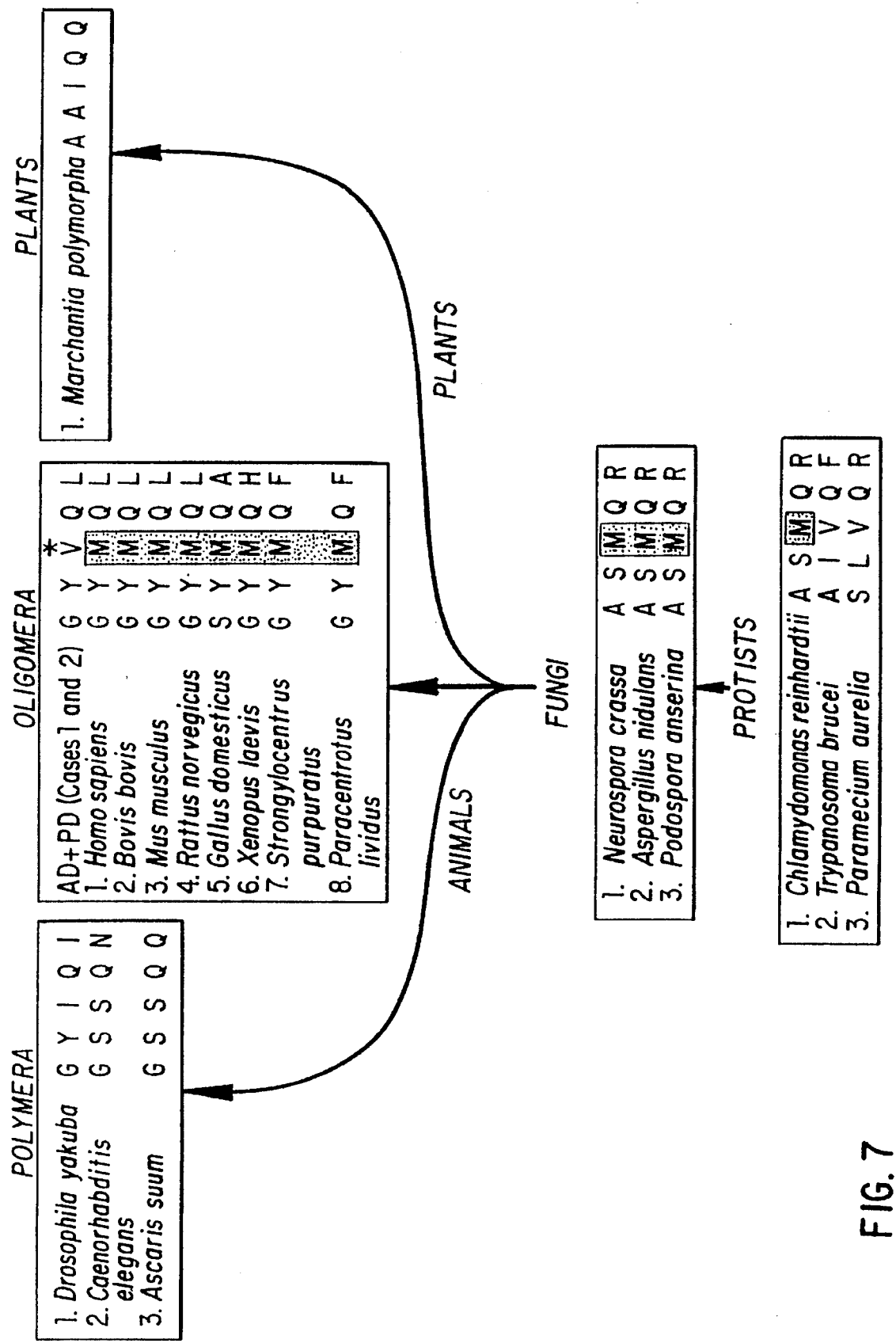

FIG. 7 shows the evolutionary conservation of methionine 31 in the human ND1 polypeptide altered by the ND$^{3,397}$ [Met→Val] mutation. The Polymera and Oligomera are the two developmental lineages of animals. The adjacent tyrosine at amino acid 30 has been proposed to be a cause of LHON$^{44}$. Shaded regions are conserved relative to the human sequence. A, alanine; F, phenylalanine; G, glycine; H, histidine; I, isoleucine; L, leucine; M, methionine; N, asparagine; Q, glutamine; R, arginine; S, serine; V, valine; Y, tyrosine. Oligomera sequences: $1^{57}$; $2^{88}$, $3^{89}$, $4^{90}$, $5^{91}$, $6^{92}$, 7, 893. Polymera sequences: $1^{94}$; 2, $3^{95}$. Plant sequence: $1^{96}$. Fungi sequences: 1, $2^{56}$, $3^{97}$. Protist sequences: $1^{98}$, $2^{56}$, $3^{96}$.

Figure 8:
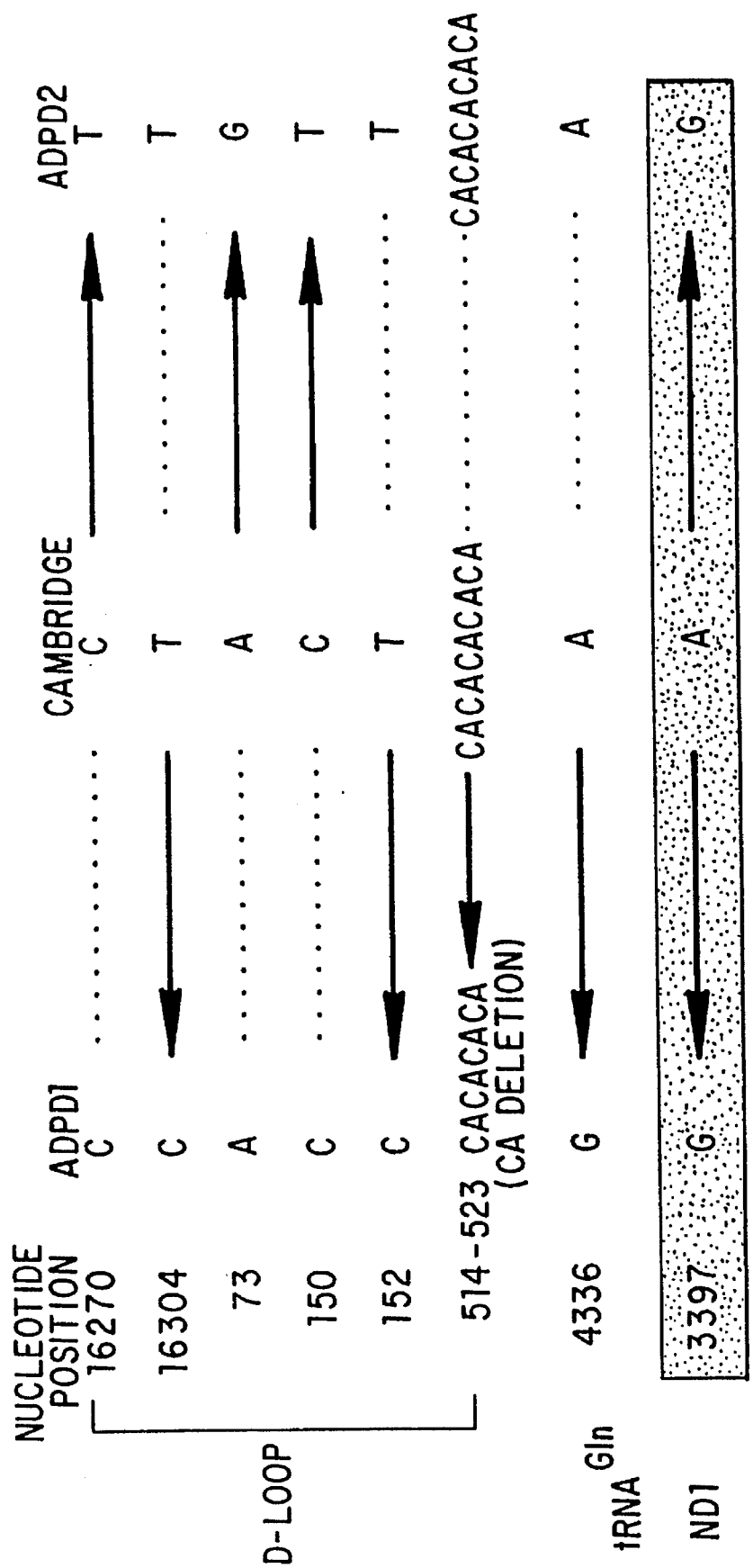

FIG. 8 shows the D-loop sequence analysis of the two AD+PD cases with the ND1$^{3,397[Met→Val]}$ mutation. Arrows designate sequence divergence of ADPD1 and ADPD2 with the standard Cambridge sequence. The nucleotides at np 4,336 in tRNA$^{Gln}$ and np 3,397 in ND1 are also indicated.

Figure 9:
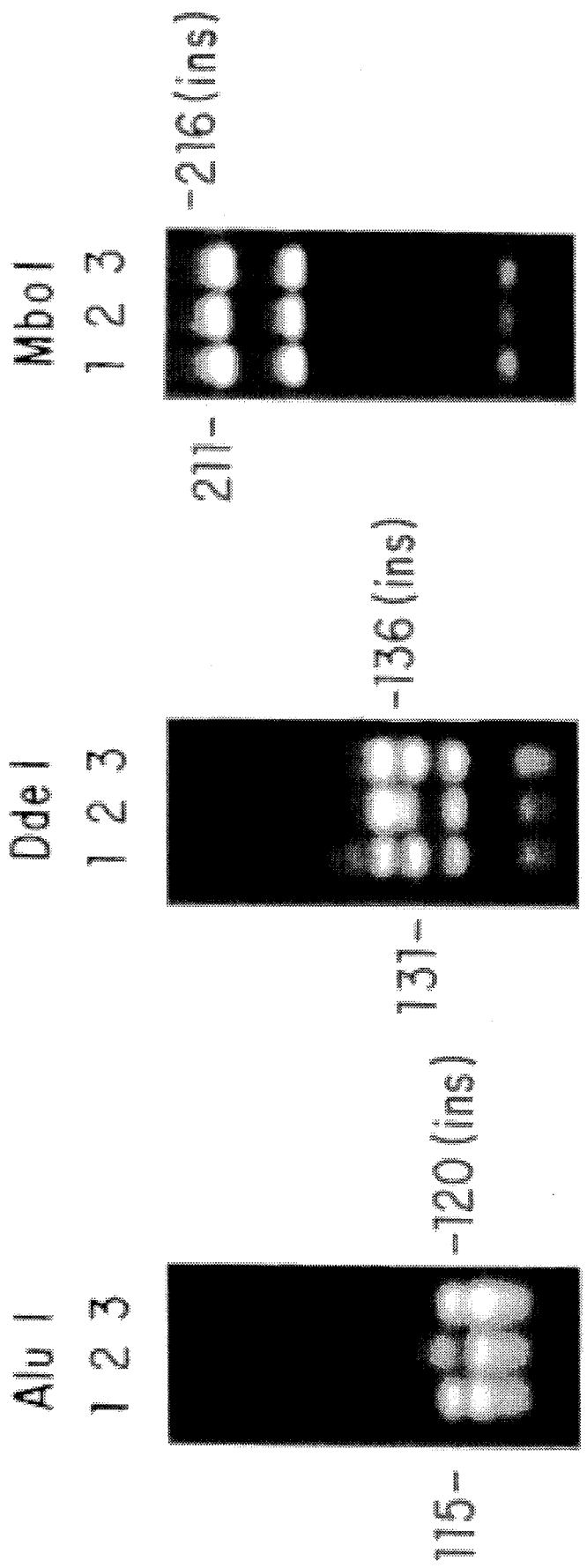

FIG. 9 shows the AluI, DdeI, and MboI digestion of a 582 np PCR fragment encompassing the 12S$^{956-965ins}$ mutation. Lanes 1 and 3 are controls showing the normal length fragment. Lane 2 ADPD29 showing approximately a five np increase in length in the normal fragments for AluI (115→ 120 nps), DdeI (131→136 nps), and MboI (211→216 nps).

Figure 10:
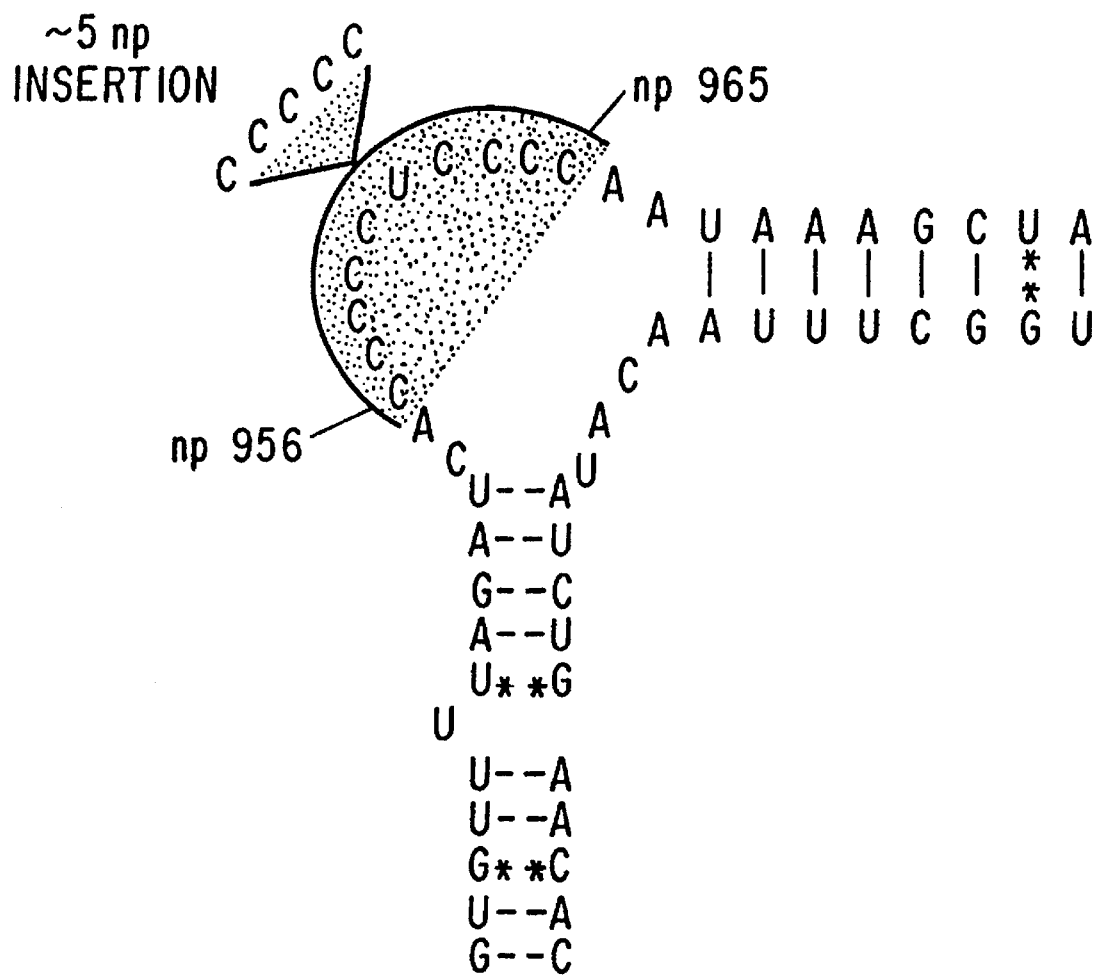

FIG. 10 shows the proposed secondary structure of the 12S rRNA gene$^{99}$ surrounding the 12S$^{956-965ins}$ insertion. The region of the insertion was determined by direct nucleotide sequencing on each strand. The precise location of the inserted Cs could not be unambiguously determined, but was localized between nps 956 and 965 (bracketed region and shaded nucleotides). Standard base pairing: lines or dashes; non-standard base pairing: asterisks.

Figure 11A:
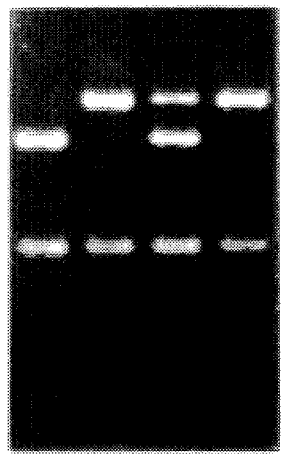
Figure 11B:
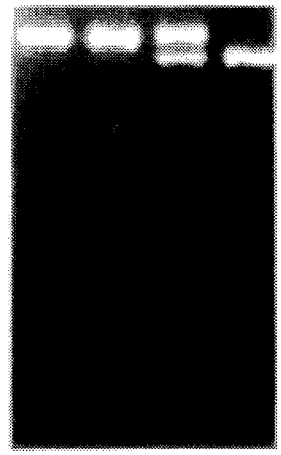
Figure 11C:
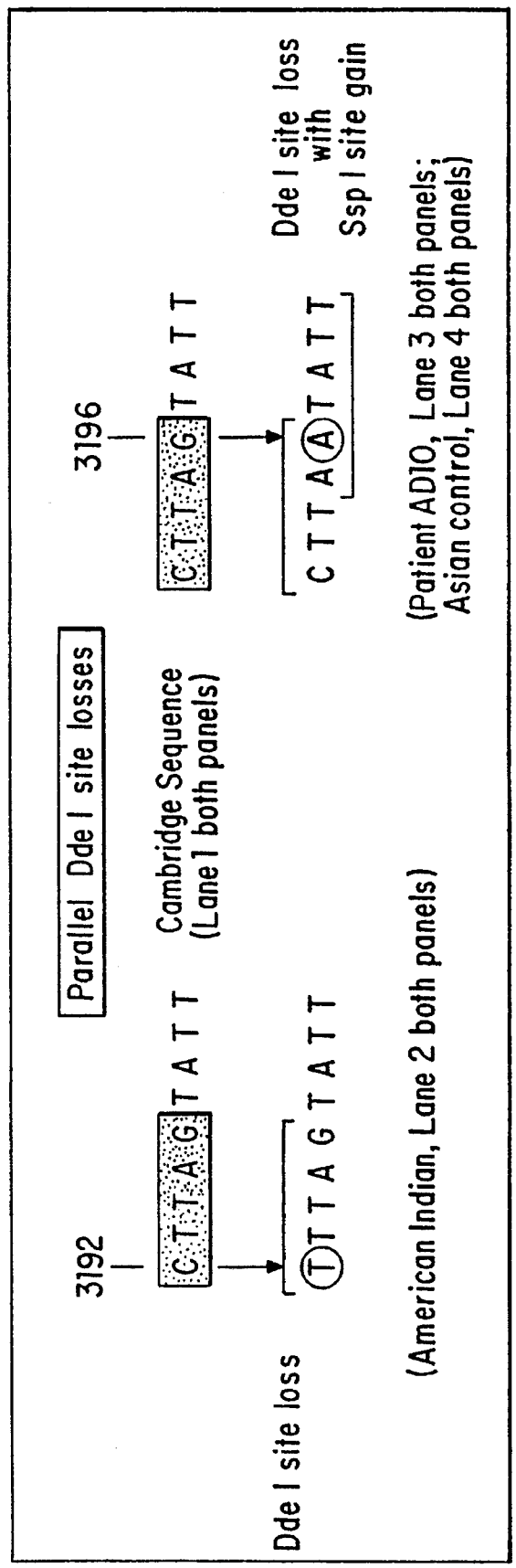

FIG. 11 shows the restriction endonuclease digests of 16S rRNA PCR fragments that identify the 16S$^{3,192}$ and 16S$^{3,196}$ mutations in patients and controls. Load order for both gels: Lane 1 is a control; 2 is the American Indian with the 16S$^{3,192}$ mutation; 3 is patient AD10 who is heteroplasmic for the 16S$^{3,196}$ mutation, and 4 is an Asian with the 16S$^{3,192}$ mutation. DdeI digests in which the presence of either the 16S$^{3,192}$ or 16S$^{3,196}$ mutation results in a site loss, changing the 342 and 194 np fragments to a 426 np fragment. SspI digests distinguish between the 16S$^{3,192}$ and 16S$^{3,196}$ mutations. A 617 np segment is cut into 530 and 87 np fragments only when the G to A 16S$^{3,196}$ mutation is present. Both the DdeI and SspI digests demonstrate the heteroplasmy in AD10 (Lane 3, both gels). The bottom panel details the relationship of the 16S$^{3,192}$ and 16S$^{3,196}$ mutations to the recognition sequences for the restriction enzymes.

Figure 12:
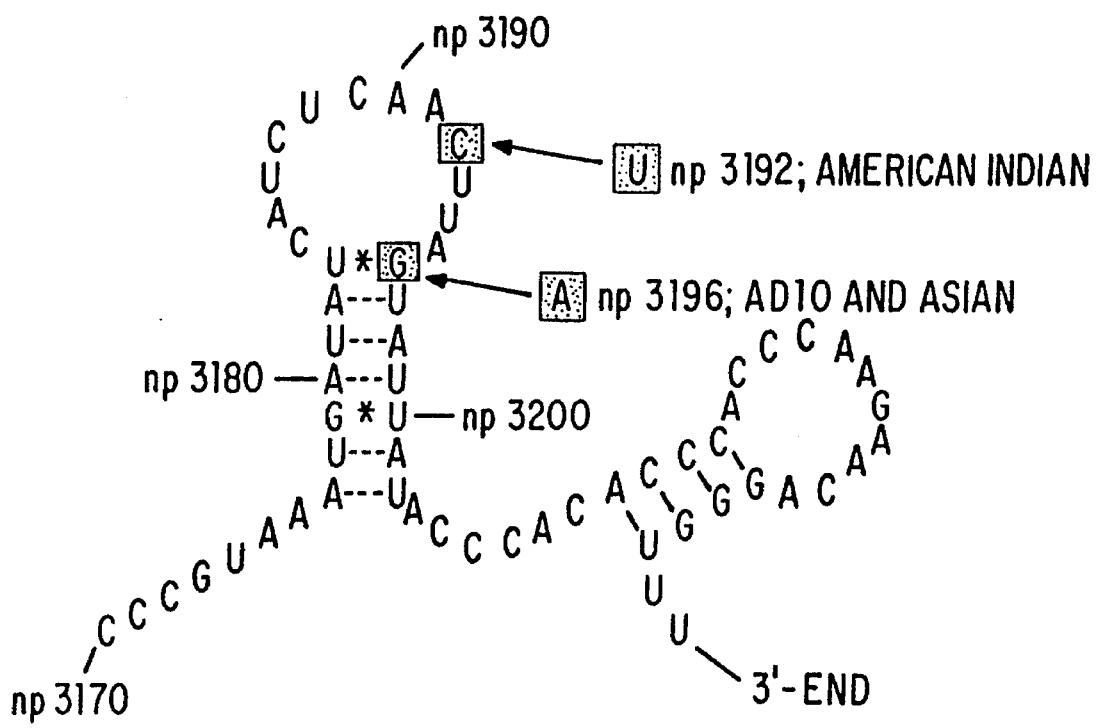

FIG. 12 shows the proposed secondary structure of the 16S rRNA at the 3'-end$^{100}$ in the region of the 16S$^{3,196}$ mutation. The polymorphic nucleotides at nps 3,192 and 3,196 are indicated by shaded boxes. Standard base pairing: lines or dashes; non-standard base pairing: asterisk.

Figure 13B:
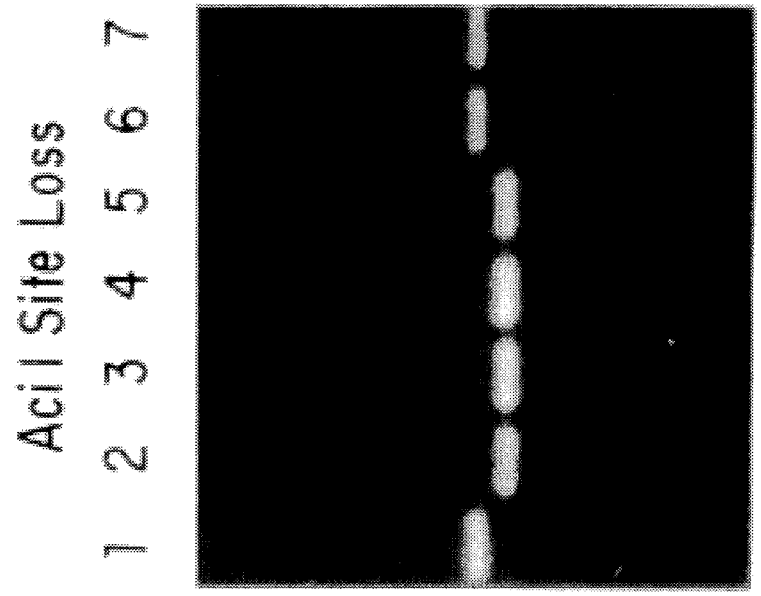
Figure 13A:
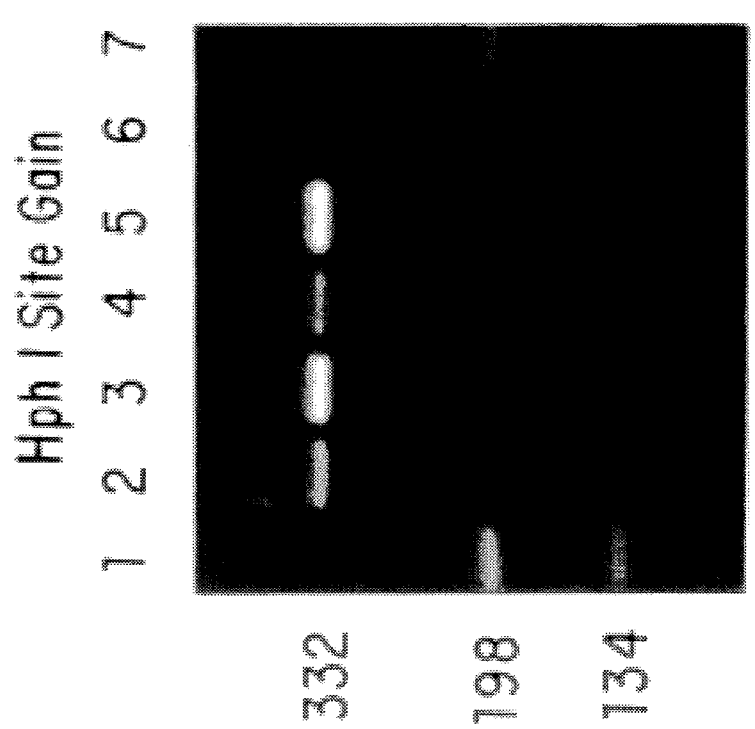

FIG. 13 shows the restriction endonuclease digests identifying the G to A ND2$^{5460}$ mutation in patients and controls. Left panel, HphI cuts the 332 np fragment to 198 and 134 np fragments in individuals with an A at np 5460. Right panel, AciI digest this fragment generated by a modified PCR primer only when there is a G at np 5460, cutting the 208 np fragment to 190 and 18 np fragments. Any nucleotide change at np 5460 eliminates this site. Load order for both panels: Lanes 2 to 5 have the Cambridge sequence$^{57}$, while lanes 1, 6, and 7 harbor the G to A mutation.

DETAILED DESCRIPTION OF THE INVENTION

This invention provides a method of diagnosing or predicting a predisposition to Alzheimer's disease and/or Parkinson's Disease. The method comprises detecting in a sample from a subject the presence of a mutation, for example, in nucleotide positions 4,336, 3,397, 3,196 or an insertion between positions 956 and 965, of mtDNA. The presence of the mutation indicates the presence of or a predisposition to Alzheimer's disease and/or Parkinson's disease. Since each mutation increases the likelihood of developing or having Alzheimer's/Parkinson's disease, the detection of more than one of the mutations in an individual can increase the probability of having or developing the disease.

The invention also provides a general method of determining mutations associated with the presence of or predisposition to Alzheimer's disease and/or Parkinson's disease. The method comprises:

(a) obtaining a mtDNA-containing sample from a subject with Alzheimer's disease;

(b) determining the presence of mutations in the mtDNA;

(c) comparing the mutations to mutations found in a normal subject; and (d) determining which mutations have a greater rate of occurrence in the subject with Alzheimer's/Parkinson's disease.

Since the clinical and neuropathological features of Alzheimer's disease and Parkinson's disease overlap extensively, the mutations can contribute to either or both diseases. Therefore, the diseases may sometimes simply be referred to herein as Alzheimer's/Parkinson's disease.

As used herein, "predicting a predisposition to Alzheimer's and/or Parkinson's disease" means determining an increased probability of developing Alzheimer's/Parkinson's disease during the subject's lifetime. Depending on the type and number of mutations correlated with the disease, it is possible to predict the likelihood of an individual developing disease. By "correlated" is meant a mutation which occurs in a higher rate in Alzheimer's/Parkinson's subjects than in normal subjects.

As used herein, "diagnosing" means using the presence of a mutation associated with Alzheimer's/Parkinson's disease as a factor in making an Alzheimer's/Parkinson's disease diagnosis. Since the presence of such mutations does not mean the subject has Alzheimer's/Parkinson's disease, the detection of the mutation is merely a step in the disease state diagnosis.

As used herein, "isolated" means free of at least some of the contaminants associated with the nucleic acid or polypeptides occurring in a natural environment.

As used herein, "nucleic acid characteristic of human mitochondrial DNA" refers to a nucleic acid which has sufficient nucleotides surrounding the codons at the mutation positions to distinguish the nucleic acid from nucleic acids encoding non-related genes. The specific length of the nucleic acid is a matter of routine choice based on the desired function of the sequence. For example, if one is making probes to detect the mutation in nt position 4,336, the length of the nucleic acid is preferably small, but must be long enough to prevent hybridization to undesired background sequences. However, if the desired hybridization is to a nucleic acid which has been amplified, background hybridization is less of a concern and a smaller probe can be used. In general, such a probe will be between 10 and 100 nucleotides, especially between 10 and 40 and preferably between 15 and 25 nucleotides in length. It is apparent to one of skill in the art that nucleotide substitutions, deletions, and additions may be incorporated into the polynucleotides of the invention. However, such nucleotide substitutions, deletions, and additions should not substantially disrupt the ability of the polynucleotide to hybridize under conditions that are sufficiently stringent to result in specific hybridization.

As used herein, the term "mutant" generally refers to a mutation in the mtDNA associated with Alzheimer's disease and/or Parkinson's disease. "Mutant" can specifically refer to a mutation at nucleotide position 4,336, 3,397, 3,196 or an insertion between positions 956 and 965 of mtDNA. For mutations at nucleotide position 4,336, 3,197 or the insertion between 956 to 965, a structural RNA is altered which will affect mitochondrial gene expression. For the mutation at nucleotide position 3,397, a codon is changed from specifying methionine to valine. Thus, other mutations which cause a change in the codon from methionine can be associated with Alzheimer's/Parkinson's disease, especially where the change is to valine.

"Specific or selective hybridization" as used herein means the formation of hybrids between a probe nucleic acid (e.g., a nucleic acid which may include substitutions, deletions, and/or additions) and a specific target nucleic acid (e.g., a nucleic acid having the mutated sequence), wherein the probe preferentially hybridizes to the specific target such that, for example, a band corresponding to the mutated DNA or restriction fragment thereof can be identified on a Southern blot, whereas a corresponding normal or wild-type DNA is not identified or can be discriminated from a variant DNA on the basis of signal intensity. Hybridization probes capable of specific hybridization to detect a single-base mismatch may be designed according to methods known in the art[124, 125, 126, 127, 128].

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential biological activity by inclusion in screening assays.

As discussed below in greater detail, the mutation can be detected by many methods. For example, the detecting step can comprise combining a nucleotide probe capable of selectively hybridizing to a nucleic acid containing the mutation with a nucleic acid in the sample and detecting the presence of hybridization. Additionally, the detecting step can comprise amplifying the nucleotides of the mutation and detecting the presence of the mutation in the amplified product. Further, the detecting step can comprise selectively amplifying the nucleotides of the mutation and detecting the presence of amplification. Finally, the detecting step can comprise detecting the loss or gain of a restriction fragment created by an enzyme digest of the nucleotides of the mutation.

Detection Techniques

Once the location of the mutations are known and associated with Alzheimer's/Parkinson's disease, the methods to detect the mutations are standard in the art. The sequence of various nucleotide probes can be determined from the known sequence of mtDNA[129], especially the sequences surrounding the mutations and insertions.

Detection of point mutations using direct probing involves the use of oligonucleotide probes which may be prepared, for example, synthetically or by nick translation. The probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. The labeled probe is reacted with a DNA sample bound to, for example, nitrocellulose under conditions such that only fully complementary sequences will hybridize. Tetra-alkyl ammonium salts bind selectively to A-T base pairs, thus displacing the dissociation equilibrium and raising the melting temperature. At 3M Me 4NCl this is sufficient to shift the melting temperature to that of G-C pairs. This results in a marked sharpening of the melting profile. The stringency of hybridization is usually 5° C. below the Ti (the irreversible melting temperature of the hybrid formed between the probe and its target sequence) for the given chain length. For 20mers the recommended hybridization temperature is about 58° C. The washing temperatures are unique to the sequence under investigation and need to be optimized for each variant.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence of the mutations, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic alteration. Alternatively, it may be possible to prepare oligonucleotides that will only bind to altered DNA, so that PCR will only result in multiplication of the DNA if the mutation is present. Following PCR, direct visualization or allele-specific oligonucleotide hybridization[130] may be used to detect the Alzheimer's/Parkinson's disease point mutation. Alternatively, an adaptation of PCR called amplification of specific alleles (PASA) can be employed; this uses differential amplification for rapid and reliable distinction between alleles that differ at a single base pair. Other techniques, such as 3SR, which utilize RNA polymerase to achieve high copy number, can also be used where appropriate.

In yet another method, PCR may be followed by restriction endonuclease digestion with subsequent analysis of the resultant products. As shown in the examples, the substitution of G for A at base pair 4,336, results in a gain of an AvaII site. The gain of this restriction endonuclease recognition site facilitates the detection of the Alzheimer's/Parkinson's disease mutation using restriction fragment length polymorphism (RFLP) analysis or by detection of the presence or absence of a polymorphic AvaII site in a PCR product that spans base pair 4,336.

For RFLP analysis, DNA is obtained, for example from the blood of the subject suspected of having Alzheimer's/Parkinson's disease and from a normal subject, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, DNA spanning an Alzheimer's/Parkinson's mutation, such as an AvaII site, is detected by determining the number of bands detected and comparing this number to the normal subject. Various restriction endonucleases can be utilized effectively for each mutation.

Similar creation of additional restriction sites by nucleotide substitutions at the disclosed mutation sites can be readily calculated by reference to the genetic code and a list of nucleotide sequences recognized by restriction endonucleases[131].

Single strand conformational analysis (SSCA)[132,133] offers a relatively quick method of detecting sequence changes which may be appropriate in at least some instances.

In general, primers for PCR and LCR are usually about 20 bp in length and the preferable range is from 15–25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms[134,135,136,137,138,139,140]. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on genetic material (or RNA) obtained from an individual, it can serve as a method of detecting the presence of the mutations.

As mentioned above, a method known as ligase chain reaction (LCR) can be used to successfully detect a single-base substitution[150,151]. LCR probes may be combined or multiplexed for simultaneously screening for multiple different mutations. Thus, LCR can be particularly useful where, as here, multiple mutations are predictive of the same disease.

Transgenic Animals and Cell Lines and Screening Methods

Having identified subjects having Alzheimer's/Parkinson's disease associated with point and insertion mutations, the subjects can be screened for an agent capable of treating Alzheimer's and/or Parkinson's disease. This method comprises administering the agent to an animal, including a human, having a mutation in mtDNA associated with Alzheimer's/Parkinson's disease and monitoring the effect of the agent on the animal's condition. If the symptoms of Alzheimer's and/or Parkinson's disease improve, the agent can be used as a treatment for the disease.

In addition, it is possible, using genetic manipulation, to develop transgenic model systems and/or whole cell systems containing the mutations for use, for example, as model systems for screening for drugs and evaluating drug effectiveness. Additionally, such model systems provide a tool for defining the underlying biochemistry of mtDNA, which thereby provides a basis for rational drug design.

One type of cell system can be naturally derived. For this, blood samples from an affected subject must be obtained in order to provide the necessary cells which can be permanently transformed into a lymphoblastoid cell line using, for example, Epstein-Barr virus. Once established, such cell lines can be grown continuously in suspension culture and may be used for a variety of in vitro experiments to study expression and processing. An alternative method for constructing a cell line is to genetically engineer the mutated gene into an established cell line of choice.

In yet a further use of the present invention, the disease mutation can be introduced into transgenic animals. For example, a mutated gene can be isolated by cloning (e.g., 1Charon35, cosmid, retrovirus or yeast artificial chromosome). The mtDNA genetic code would be altered by in vitro mutagenesis to create a mRNA compatible with the nuclear-cytosol system. A mitochondrial targeting sequence would then be added to the amino terminal end by gene splicing from a nuclear OXPHOS gene such as the β subunit of the ATP synthase. The chimeric gene could be inserted in an appropriate nuclear vector. Alternatively, the gene could be inserted into a mitochondria-specific vector. The vector could be transferred or inserted into the cell or animal and the products screened for appropriate integration. As a result of the transfer, the resultant transgenic non-human animal will express the Alzheimer's/Parkinson's genes.

One approach to creating transgenic animals is to mutate the animal mtDNAs by in vivo mutagenesis, transfer the mutant mtDNA into the mitochondrial embryonic stem cells by DNA transfection and injection of the embryonic stem cells into blastocysts to prepare allophenic mice carrying the disease causing mtDNA mutation[152]. Alternatively, the technique of microinjection of the mutated gene or mitochondria, into a one-cell embryo followed by incubation in a foster mother can be used. Certain possibilities for the general use of transgenic animals are disclosed[153,154,155,156,157]. Alternatively, viral vectors, e.g., Adeno-associated virus, can be used to deliver the mutated gene to the stem cell. In addition, such viral vectors can be used to deliver the mutated gene to a developed animal and then used to screen[158,159].

To more accurately model the disease, transgenic animals can be created with a combination of multiple mutations, e.g. 4,336, 3,397, 3,196 or the insertion mutation, in the same animal produced by the technologies described above can be utilized. Similarly, cell lines manipulated to include several mutations will be of value in modeling the disease and are an important consequence of this invention.

Gene Therapy

Having detected the genetic mutation in the mitochondrial gene sequence in an individual, it is possible to employ gene therapy, in the form of gene implants, to prevent the development of the disease. In the present case, if significant mutations in the mtDNA are discovered, the nucleus from the egg of a carrier mother can be inserted into an egg having normal mtDNA from which the original nucleus has been removed. The egg can then be reintroduced into the mother. Such a method can be utilized to delete any mutation of the mtDNA while maintaining the genes from the mother which affect appearance.

Antibodies and Recombinant Expression of Mutant Polypeptides

When the mutated oxphos gene product is a polypeptide, e.g. the 3,397 mutation, it can be used to prepare antisera and monoclonal antibodies using, for example, the method of Kohler and Milstein[160]. Such monoclonal antibodies could then form the basis of a diagnostic test.

Such variant polypeptides can also be used to immunize an animal for the production of polyclonal antiserum[161]. For example, a recombinantly produced fragment of a variant polypeptide can be injected into a mouse along with an adjuvant so as to generate an immune response. Murine immunoglobulins which bind the recombinant fragment with a binding affinity of at least $1\times10^7$ m$-1$ can be harvested from the immunized mouse as an antiserum, and may be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1\times10^6$ M$-1$. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant but not wild-type.

The nucleic acid sequences of the present invention capable of ultimately expressing the desired variant polypeptides can be formed from a variety of different polynucleotides (genomic or cDNA, RNA, synthetic oligonucleotides, etc.) as well as by a variety of different techniques.

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art[124]. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

E. coli is one prokaryotic host useful particularly for cloning DNA sequences of the present invention. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation.

Other microbes, such as yeast, may also be used for expression. Saccharomyces can be a suitable host, with suitable vectors having expression control sequences, such as promoters, including 3-phosphoglycerate kinase or other glycolytic enzymes, and an origin of replication, termination sequences etc. as desired.

In addition to microorganisms, mammalian tissue cell culture may also be used to express and produce the polypeptides of the present invention[162]. Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer[163], and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest (e.g., polypeptides encoding a variant polypeptide) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Kits

The method lends itself readily to the formulation of test kits which can be utilized in diagnosis. Such a kit would comprise a carrier compartmentalized to receive in close confinement one or more containers wherein a first container may contain suitably labeled DNA probes. Other containers may contain reagents useful in the localization of the labeled probes, such as enzyme substrates. Still other containers may contain restriction enzymes (such as RsaI), buffers etc., together with instructions for use.

Analysis of Mutations

Three lines of evidence suggest that the $tRNA^{Gln4,336}$ mutation defines an mtDNA lineage which is associated with an increased risk for manifesting Alzheimer's disease and Parkinson's disease. First, the $tRNA^{Gln4,336}$ mtDNA lineage correlates with the Alzheimer's disease and Parkinson's disease phenotype, being found 7.4 times more frequently in Caucasian patients than in Caucasian controls. Second, Alzheimer's disease and Parkinson's disease patients cluster in the $tRNA^{Gln4,336}$ lineage, suggesting that these clinical phenotypes are linked to this mtDNA haplotype. Third, the $tRNA^{Gln4,336}$ lineage has been found to harbor two additional novel and potentially pathogenic mutations, the $ND1^{3,397[Met \rightarrow Val]}$ missense mutation and the $12S^{956-965ins}$ insertion. Since multiple, sequential, rare events are more likely to cluster together if they are functionally related[42], the accumulation of these three mtDNA mutations in an Alzheimer's disease and Parkinson's disease mtDNA lineage demonstrates that these mutations act synergistically to increase the risk of manifesting these diseases.

The $ND1^{3,397[Met \rightarrow Val]}$ mutation has a number of features which demonstrate that it also contributes to Alzheimer's disease and Parkinson's disease pathology. First, the mutation changes the highly conserved methionine at codon 31 in the ND1 polypeptide to a valine. This mutation is immediately adjacent to the $ND1^{3,394[Tyr \rightarrow His]}$ mutation in codon 30 that has been found in a rare form of LHON[44]. Therefore, mutations in this region of ND1 appear to be pathologically significant. Second, the $ND1^{3,397[Met \rightarrow Val]}$ mutation is maternally inherited and maternal relatives of pedigrees harboring this mutation have also been found to manifest clinical features of Alzheimer's disease. Third, the mutation has arisen two independent times in Caucasian patients, but has not been found in 248 Caucasian controls, demonstrating that in Caucasians it is associated with AD+PD pathology.

The $12S^{956-965ins}$ insertion was found in an AD+PD patient (ADPD29) within the $mtDNA^{16,304+336}$ lineage. Although small insertions occur commonly in the non-coding regions of the $mtDNA^{55}$, nucleotide insertion mutations have not been observed within mtDNA genes. This observation was affirmed by the absence of the $12S^{956-965ins}$ mutation in 699 individuals from various ethnic groups. Thus, while the unique nature of this event precludes calculation of its statistical significance, the location of the insertion within an OXPHOS gene that is essential to protein synthesis, its absence in all controls, and its association with the rare $tRNA^{Gln4,336}$ mutation demonstrates that it can be functionally related to the AD+PD phenotype.

Each of the four mtDNA mutations identified in this study can result in OXPHOS defects similar to those reported in Alzheimer's disease and Parkinson's disease patients. Defects in respiratory Complexes I and IV have been reported for PD[17,18], in Complex I for PD[13-16,18], and in Complex IV for PD[18] and AD[19]. The $tRNA^{Gln4,336}$ and $12S^{956-965ins}$ mutations would be expected to impair mitochondrial protein synthesis and thus affect Complexes I and IV, as observed for the $tRNA^{Lys8,334}$ mutation that causes MERRF[31,32], the $tRNA^{Leu3,260}$ mutation that causes maternally inherited mitochondrial myopathy and cardiomyopathy[78], and the $tRNA^{Leu3,243}$ mutation that causes MELAS[74]. The $ND1^{3,397[Met \rightarrow Val]}$ mutation could cause defects in Complex I as observed for the LHON $ND1^{3,460[Ala \rightarrow Thr]}$ mutation[121], the $ND1^{4,160[Leu \rightarrow Pro]}$ mutation[123], and the $ND4^{11,778[Arg \rightarrow His]}$ mutation[121,122].

The clustering of the $tRNA^{Gln\ 4,336}$, the $12S^{956-965ins}$, and the $ND1^{3,397[Met \rightarrow Val]}$ mutations on the $mtDNA^{16,304+4,336}$ lineage is analogous to the accumulation of multiple mtDNA mutations in LHON[11,12,42,44]. This demonstrates that several, mildly deleterious mtDNA mutations can accumulate within an mtDNA lineage and act synergistically to cause Alzheimer's disease and Parkinson's disease. The cumulative OXPHOS defect produced by these mutations can be further exacerbated by the age-related decline in OXPHOS function resulting from the accumulation of somatic mtDNA mutations in stable tissues[11,12]. As the severity of the inherited OXPHOS defect increases, the neuronal ATP generating capacity would decline, increasing the probability of falling below the expression threshold and causing the Alzheimer's disease or Parkinson's disease phenotype[11,12].

The probabilistic nature of this model means that individuals who inherit mildly deleterious mtDNA mutations, such as the $tRNA^{Gln4,336}$ mutation, will only occasionally manifest disease symptoms, and appear as seemingly sporadic cases. This is comparable to the situation for the LHON mutations at position 15,257 in the cytochrome b gene and position 7,444 in the COI gene[42,51]. By contrast, individuals inheriting more severe mtDNA mutations or combinations of mutations such as $tRNA^{Gln4,336}$ plus $ND1^{3,397[Met \rightarrow Val]}$ who have greater reductions in neuronal ATP generating capacity and thus be more likely to have affected maternal relatives. Other genetic and environmental factors could also influence the neuronal OXPHOS capacity and increase the likelihood of disease expression. Genetic factors could include nuclear genes similar to the X-linked gene proposed to influence LHON expression[47], and some of the loci affecting Alzheimer's disease and Parkinson's disease might be nuclear encoded OXPHOS genes[11,12].

Throughout this application various publications are referenced. The disclosures of these publications in their entireties are hereby incorporated by reference into this application in order to more fully describe the state of the art to which this invention pertains.

The following examples are intended to illustrate but not limit the invention. While they are typical of those that might be used, other procedures known to those skilled in the art may be alternatively employed.

EXAMPLES

Patient and Control Samples

The AD plus PD samples included 73 autopsy brains with neuropathological changes of AD+PD[4], 62 brains with the conventional changes of AD[5,81] and 38 blood and muscle samples collected from Parkinson's disease patients responsive to levodopa. The age range for these groups of individuals was approximately 51 to 91 years. One brain included in the Alzheimer's disease group which harbored the tRNA$^{Gln4,336}$ mutation was originally considered borderline for classification in the Alzheimer's disease group based on number of plaques for age. However, further analysis, which included staining of sections with the Alzheimer-50 antibody and silver staining, identified a significant accumulation of neuritic plaques and neurofibrillary tangles and was felt to be consistent with early Alzheimer's disease. Therefore, this case was included in the patient group. However, either exclusion or inclusion of this patient in the analysis did not alter the p-values. All p-values were calculated using the Pearson Chi-square, Yates corrected Chi-square, and Fisher exact (two tail) method[82].

Additional pathological samples included blood and muscle samples from three patients with multisystems atrophy and one with progressive supranuclear palsy, and brain samples from two patients with amyotrophic lateral sclerosis, one with MELAS, two with multiple sclerosis, one with mental retardation, epilepsy and short stature, and one with Leigh's disease. Control samples included 23 brains with no observed neuropathology, and 547–699 blood and placental samples examined in our laboratory.

Phylogenetic Analysis

Genomic DNA was isolated from brains frozen at autopsy, platelets, or skeletal muscle as previously described[38]. For haplotype analysis, the entire mtDNA genome was amplified as nine overlapping fragments by polymerase chain reaction (PCR) and surveyed for restriction fragment length polymorphisms by digestion with the following 14 restriction endonucleases. AluI, AvaII, BamHI, DdeI, HaeII, HaeIII, HhaI, HinfI, HincII, HpaI, HpaII, MboI, RsaI, TaqI[18,42,54]. These PCR fragments were generated with the following forward → and reverse ← primer pairs and PCR annealing temperature ($T_H$): (1) nps 1562–1581→; 3701–3717← ($T_H$=51° C.), (2) nps 3007–3023→, 5898–5917← ($T_H$=55° C.), (3) nps 5317–5333→, 7588–7608← ($T_H$=57 ° C.), (4) nps 7392–7410→, 8902–8921← ($T_H$=57° C.), (5) nps 8282–8305→, 10,088–10,107← ($T_H$=57° C.), (6) nps 9911–9932→, 11,851–11,873← ($T_H$=69° C.), (7) nps 11,673–11,691→, 13,932–13,950← ($T_H$=57° C.), (8) nps 13,914–13,930→, 16,527–16,547← ($T_H$=47° C.), (9) nps 16,453–16,472→, 1677–1696← ($T_H$=61° C.). Restriction fragments were resolved by electrophoresis on 1.0–2.5% NuSieve plus 1.0% SeaKem agarose (FMC BioProducts) gels, visualized by ethidium bromide staining and mapped by the sequence comparison method[57,83,84]. The composite restriction map which represents individual haplotypes is given in the legend of FIG. 1.

The evolutionary relationship among the 71 AD, AD+PD, and PD patients and 74 Caucasian controls plus the Cambridge sequence[57] was inferred using parsimony analysis with the computer program PAUP[85]. An African mtDNA haplotype from a Senegalese was used to root the resulting phylogenetic tree. Sequence divergence between haplotypes was estimated by a maximum likelihood procedure using the computer program DREST[86]. The divergence rate used to assess restriction site variation was 2–4% per million years[58]. For the D-loop sequence analysis, only those nucleotide positions unambiguously sequenced and shared by the individuals being compared were included in divergence time calculations (900 total nucleotides for the ND1$^{3,397}$ $^{[Met \to Val]}$ mutation and 344 total nucleotides for individuals with the tRNA$^{Gln4,336}$ mutation). The divergence rate used to assess differences in the D-loop sequence between individuals was 8.4% per million years[87].

DNA Sequencing

D-loop sequencing and sequencing of mutations identified by phylogenetic analysis were performed using previously described direct sequencing protocols[31,39,42].

A D-loop PCR segment was generated from primers positioned at either nps 15,705–15,723→ and nps 221–240← ($T_H$=47° C.) or nps 15,243–15,259→ and nps 1467–1486← ($T_H$≦45° C.). Asymmetric PCRs were generated from this fragment for sequencing using the following primer pairs: (1) nps 15,704–15,723→ and 16,344–16,364← ($T_H$=49° C.), (2) nps →5,794–15,813→ and 16,527–16,547← ($T_H$=51° C.), (3) nps 16,141–16,160→ and 408–429← ($T_H$=53° C.), (4) nps 16,141–16,160→ and 16,401–16,420← ($T_H$=53° C.), (5) nps 16,141–16,160→ and 16,527–16,547← ($T_H$=51 ° C.), (6) nps 15,978–15,996→ and 16,527–16,547← ($T_H$=55° C.), (7) nps 16,141–16,160→ and 408–429← (TH=53° C.), (8) nps 1–20→ and 408–429← ($T_H$=55° C.), (9) nps 1–20→ and 1227–1246← ($T_H$=51° C.), (10 ) nps 247–264→ and 751–770← ($T_H$=51° C.), (11) nps 242–261→ and 751–770← ($T_H$53 ° C.). The following primers were used to sequence the D-loop from the single stranded mtDNA generated by the asymmetric PCR: (1) nps 15,978–15,997, (2) nps 16,028–16,047, (3) nps 16,225–16,244, (4) nps 16,287–16,306, (5) nps 16,364–16,344, (6) nps 16,401–16,421, (7) nps 16,527–16,547, (8) nps 131–150, (9) nps 242–261, (10) nps 371–390, (11) nps 617–636.

The tRNA$^{Gln4,336}$ mutation was amplified within a 2.9 kb PCR fragment generated from primer pair 2 in the phylogenetic analysis. Single stranded mtDNA was generated using nested primers at nps 3941–3970→ and 5049–5067← ($T_H$=53° C.) and sequenced with a primer at nps 4201–4219.

The ND1$^{3,397(Met \to Val)}$ mutation was sequenced from a 1.4 kb mtDNA fragment amplified with primers at nps 3108–3127 (→) and 4489–4508 (←) ($T_H$=53° C.). Single stranded mtDNA was generated using primers at nps 3108–3127 (→) and 3701–3717 (←) ($T_H$=51° C.) and sequenced with a primer at nps 3317–3337.

Attempts to define the sequence of the 12S$^{956-965ins}$ mutation were made using a mtDNA fragment amplified with primers at nps 1–20→ and 1696–1677← ($T_H$=55° C.). Numerous asymmetric PCR reactions were prepared and the sequencing primers used were located at nps 811–831, 871–890, and 1064–1045. The 12S956–965ins mutation was localized with this approach to the mtDNA sequence between nps 956 and 965. However, the precise mtDNA sequence within this region which contains nine cytosines in the Cambridge sequence[57] could not be unambiguously ascertained. The best interpretation of the sequencing gels in this region is an insertion of approximately five cytosines.

The $16S^{3,192}$ and $16S^{3,196}$ mutations were sequenced from a 2.9 kb PCR fragment generated from primer pair 2 of the phylogenetic analysis. Single stranded mtDNA was generated using primers at nps 3007–3023→ and 3701–3717← ($T_H$=51° C.) and sequenced with a primer at nps 3108–3127.

Restriction Endonuclease Screening for Point Mutations

Restriction endonuclease screening of patient and control mtDNAs was performed using AvaII for the $tRNA^{Gln4,336}$ mutation; RsaI for the $ND1^{3,397[Met \to Val]}$ mutation; AluI, DdeI, and MboI for the $12S^{956-965ins}$ mutation; DdeI and SspI for the $16S^{3,196}$ mutation; and AciI and HphI for the $ND2^{5460}$ mutation. Digestions were performed under standard conditions and separated on either on 2.5–2.8% NuSieve agarose plus 0.8–0.9% SeaKem agarose gels. Fragments were visualized by ethidium bromide fluorescence.

To screen for the AvaII site gain produced by the $tRNA^{Gln4,336}$ mutation in patients and controls, a 578 np segment of the mtDNA was amplified at $T_H$=55° C. with primers at nps 3951–3970 plus a 10 np tail → and 4489–4508 plus a 10 np tail ←. The normal sequence remains undigested while those containing the $tRNA^{Gln4,336}$ mutation are cleaved, giving fragments at 395 and 183 nps. A 1142 nps segment of the mtDNA was amplified for FIG. 3 using primers at nps 3598–3615→ and 4720–4739←. The normal sequence remains undigested giving a fragment of 1142 np, while the $tRNA^{Gln4,336}$ mutation yields fragments at 735 and 407 nps.

The RsaI site gain produced by the $ND1^{3,397[Met \to Val]}$ mutation was evaluated by amplifying a 730 np segment of the ND1 gene at $T_H$=50° C. with primers at nps 3007–3023 plus a 9 np tail (→) and 3701–3717 plus a 10 np tail (←). Sizes of the digestion products for the normal sequence were 390, 214, and 126 nps and for the mutant containing $ND1^{3,397[Met \to Val]}$ were 329, 214, 126, and 61 nps.

The $12S^{956-965ins}$ mutation was detected by multiple restriction endonuclease digestions including AluI, DdeI, and MboI. The 582 np segment of mtDNA containing the $12S^{956-965ins}$ mutation was amplified at $T_H$=51° C. using primers at nps 664–683→ and 1227–1246←. AluI digestion of mtDNA with the Cambridge sequence produced fragments with sizes of 115, 101, 96, 90, 85, 80, and 11 nps. The $12S^{956-965ins}$ mutation increased the 115 np fragment to approximately 120 nps. DdeI digestion produced fragments with sizes of 153, 131, 76, 72, 35, 15, and 9 nps. The $12S^{956-965ins}$ mutation increased the 131 np fragment to approximately 136 nps. MboI digestion produced fragments with sizes of 276, 211, 76, and 19 nps. The $12S^{956-965ins}$ mutation increased the 211 np fragment to approximately 216 nps.

The $16S^{3,192}$ and $16S^{3,196}$ mutations were evaluated using a 617 np segment of the mtDNA amplified at $T_H$=51° C. with primers at nps 3108–3127→ and 3701–3717 plus a 10 np tail ←. DdeI digestion resulted in a site loss when either the C to T mutation at np 3,192 or the G to A mutation at np 3,196 were present. Sizes of the digestion products for the normal sequence were 342, 194, and 84 nps and for the sequence containing either the $16S^{3,192}$ or $16S^{3,196}$ mutations were 426 and 194 nps. SspI digestion revealed a site gain only when the G to A mutation at np 3,196 was present. The normal sequence remained uncut at 617 np, while the mutant $16S^{3,196}$ was divided into 530 and 87 np fragments.

The $ND2^{5460}$ G to A and G to T mutations were evaluated by several methods. To test for the G to A mutation, a 2820 np segment of mtDNA was amplified at $T_H$=53° C. with primers at nps 3108–3127→ and 5898–5917 plus a 10 np tail ← or a 332 np segment of mtDNA at $T_H$=49° C. with primers at nps 5317–5333→ and 5629–5648←. Digestion of the 2820 np segment with HphI gave 13 fragments ranging in size from 12 to 1130 np. A 491 np fragment located at nps 5315–5806 contained np 5460 and remains uncut with the Cambridge sequence, but was cut into 346 and 145 np fragments when the G to A nucleotide change was present. When the 332 np mtDNA segment was digested with HphI, it remained uncut when the Cambridge sequence was present and was cut into 198 and 134 np fragments when the G to A mutation was present (FIG. 13). The second method was specific for the G to T mutation at np 5460. A primer was constructed with a mismatched "G" at np 5458 that created an AluI site only when the mutant T at np 5460 was present (mismatch primer sequence at nps 5441–5459: 5'-ATTCCTCCCCACACTCA"G"C-3' [SEQ ID No:1]). A 487 np segment of mtDNA was amplified at $T_H$=49° C. with the mismatch primer → and a primer at nps 5898–5917 plus a 10 np tail ←. Digestion with AluI produced fragments with sizes of 144, 104, 82, 60, 53, and 44 np for the Cambridge sequence and sizes of 125, 104, 82, 60, 53, 44, and 19 if the T at np 5460 was present. The third method was specific for the Cambridge sequence G at np 5460. A primer was constructed with a mismatched "C" at np 5458 that created an AciI site only when the Cambridge sequence "G" at np 5460 was present (mismatch primer sequence at nps 5441–5459: 5'-ATTCCTCCCCACACTCA"C"C-3' [SEQ ID NO:2]). A 208 np segment of mtDNA was amplified at $T_H$=49° C. with the mismatch primer → and a primer at nps 5629–5648← (FIG. 13) or a 487 np segment of mtDNA was amplified at $T_H$=49° C. with the mismatch primer → and a primer at nps 5898–5917 plus a 10 np tail ←. Digestion with AciI of PCR segments containing the Cambridge sequence G at np 5460 produced fragments with sizes of 190 and 18 np for the 208 np segment and sizes of 278, 173, 18, 15, and 3 np for the 487 np segment. Any nucleotide change at np 5460 resulted in no cut in the 208 np fragment and fragments with sizes 296, 173, 15, and 3 for the 487 np segment.

RESULTS

Phylogenetic Analysis of mtDNA Mutations in AD, AD+PD, and PD

To identify mtDNA mutations that may be associated with Alzheimer's disease and Parkinson's disease, we determined the restriction endonuclease site patterns (haplotypes) of the mtDNAs from a group of 71 Caucasian patients, consisting of 33 with AD, 30 with AD+PD, and 8 with PD, as well as 74 Caucasian controls. Each mtDNA genome was amplified in nine overlapping polymerase chain reaction (PCR) fragments and each fragment was digested with 14 restriction endonucleases. Restriction site changes were detected by agarose gel electrophoresis and the phylogenetic relationships of the patient and control mtDNA haplotypes determined by the parsimony program PAUP[18,42,53,54]. Novel restriction site variants were identified by comparing the patients' restriction site variants with those of our global data base for mtDNA restriction site polymorphisms[55].

Nine patients (two with AD, five with AD+PD, and two with PD) and one control were found to harbor an Rsa I site loss in the mtDNA D-loop at np 16,304, a region with no known function, and an Ava II site gain at np 4,336 which occurs in the tRNA$^{Gln}$ gene (tRNA$^{Gln4,336}$). The combination of these mutations caused these patients to cluster on one discrete branch of the Caucasian mtDNA phylogeny (FIG. 1; bold lines). Within this mtDNA$^{16,304+4,336}$ lineage, two additional novel mtDNA mutations were found. One of these was an Rsa I site gain in ND1 at np 3,397 found in patient ADPD1. This same mutation was also found in patient ADPD2 outside the mtDNA$^{16,304+4,336}$ lineage (FIG. 1, enclosed by a box). The second novel mutation found in the mtDNA$^{16,304+4,336}$ lineage was an insertion of approximately five nucleotides between nps 956 and 965 in the 12S rRNA gene of patient ADPD29. A third novel mutation was found outside the mtDNA$^{16,304+4,336}$ lineage in patient AD10 (FIG. 1, enclosed by a box). This individual harbored a heteroplasmic Dde I site loss at np 3,196 in the 16S rRNA gene.

The tRNA$^{Gln4,336}$ Mutation

To substantiate the clustering of the nine AD and PD mtDNAs within the mtDNA$^{16,304+4,336}$ lineage, we sequenced 344 nps of the D-loop hypervariable region from each patient. Consistent with their forming a single mtDNA lineage, all were found to harbor the T to C transition at np 16,304, thus eliminating the Rsa I site. Two mtDNAs, ADPD28 and AD23, also had a second T to C transition at np 16,311 which eliminated an adjacent Rsa I site and ADPD28 also had a T to C transition mutation at np 16,172. Thus, all nine patients had very similar D-loop sequences, confirming that they belonged to the same mtDNA lineage. Divergence calculations using the observed D-loop and restriction site polymorphisms suggest that the tRNA$^{Gln4,336}$ mutation arose in a Caucasian mtDNA 8,500 to 17,000 years ago.

To investigate the relationship of the tRNA$^{Gln4,336}$ mutation to Alzheimer's disease and Parkinson's disease, we sequenced the tRNA$^{Gln}$ gene from three of the patient mtDNAs. This revealed that all harbored the A to G transition mutation at np 4,336 necessary to create the Ava II site (FIGS. 2 and 3). This nucleotide connects the amino acid acceptor stem with the TΨC stem and is conserved in human, cow, and chicken mtDNAs, but not in mouse and Xenopus (FIG. 4). The mutation was present in 3.2% (2/62) of brains with Alzheimer's disease, 6.8% (5/73) of brains with AD+PD, and 5.3% (2/38) of patients who were clinically defined as having Parkinson's disease, giving an overall total of 5.2% (9/173) of the patients examined in this study (Table I). By contrast, the tRNA$^{Gln4,336}$ mutation was present in 0.2% (1/547) of individuals analyzed in our population studies (laboratory controls) (see Table I legend for references).

Additional control data was obtained from published population surveys of mtDNA restriction site variants in which Ava II digestion was included (literature controls) (see Table I legend for references). This analysis revealed that this Ava II site gain has not been observed in Africans, Asians, or American Indians, but was reported infrequently in Caucasians (Table I). Since virtually all of the AD, AD+PD, and PD patients studied were Caucasian and the tRNA$^{Gln4,336}$ mutation arose in a Caucasian mtDNA lineage, we compared the patient frequency of this Ava II site gain with that of all Caucasians surveyed to date. This analysis yielded a control frequency of 0.7% (12/1691) which includes 125 laboratory controls and 1566 literature controls. Compared to this frequency, the tRNA$^{Gln4,336}$ mutation was 4.6 times more common in AD patients, 9.7 times more common in AD+PD patients, 7.6 times more common in PD patients, and 7.4 times more common in all AD and PD patients than in the Caucasian controls. While the number of patients who harbored the tRNA$^{Gln4,336}$ mutation for the Alzheimer's disease (2/62) and PD (2/38) groups was too small to insure valid statistical comparisons, the AD+PD patients (5/73) and the combination of all AD, AD+PD, and PD patients (9/173) showed a statistically significant difference from the frequency of the tRNA$^{Gln4,336}$ mutation observed in the total Caucasian control group at the p<0.005 level. Similarly, comparison of the AD+PD or the total patient groups with all controls examined (12/3138 or 0.4%) was significant at p<0.005. Thus, individuals harboring the tRNA$^{Gln4,336}$ mutation appear to be at an increased risk for developing AD, AD+PD, or PD.

The observed frequency difference between the Caucasian patients and controls was not due to a sampling bias in which a subpopulation with an increased frequency of the tRNA$^{Gln4,336}$ mutation was over-represented in our patient population, since we observed this mutation at increased frequency in patients from three different regions of the United States: Massachusetts 2/68 (2.9%), Georgia and North Carolina 4/82 (4.8%), and southern California 3/23 (13%). Moreover, the Caucasian controls analyzed in our laboratory and those from the literature included random Californians and Georgians, British, Finnish, Italians, Jews, Arabs and Hindus, and none of these populations had significantly increased frequencies of tRNA$^{Gln4,336}$ mutation relative to the population average (Table I, legend). Consequently, if a sampling bias did exist for our patients, it occurred independently in each of three different regions of the United States, and the increased input of the tRNA$^{Gln4,336}$ mtDNAs would have had to come from an immigrant population which was a minor contributor to American colonization. Therefore, it seems most likely that the increased frequency of the tRNA$^{Gln4,336}$ mutation in our Alzheimer's disease and Parkinson's disease patients was due to increased pathology rather than sampling error.

The ND1$^{3,397[Met \rightarrow Val]}$ Mutation

To characterize the Rsa I site gain in ND1 which was found in ADPD1 within the mtDNA$^{16,304+4,336}$ lineage and ADPD2 located outside this lineage, we sequenced this region of the mtDNA from these patients as well as from three controls. An A to G transition mutation was found at np 3,397 in all cases (FIGS. 5 and 6). This mutation substituted a valine for a methionine at the thirty-first amino acid in the ND1 protein. This methionine has been conserved throughout animal Oligomera evolution, extending down to fungi and some protozoa. It diverges in the invertebrate Polymera lineage and in plants (FIG. 7, shaded area). Further, the ND1$^{3,397[Met \rightarrow Val]}$ mutation alters a highly conserved methionine within a hydrophilic block of 36 amino acids that is conserved from *Trypanosoma brucei* to man[56]. Thus, this mutation could be functionally significant.

This mutation was found in two of the 73 AD+PD brains examined (2.7%). It was not found in 62 AD brains, 38 blood samples from clinically ascertained Parkinson's disease patients, or 11 brain samples from patients with other CNS diseases (Table II). Since the two AD+PD patients which harbor the ND1$^{3,397[Met \rightarrow Val]}$ were Caucasian, we investigated the frequency of this mutation in Caucasian controls. No positives were found in 90 Caucasian laboratory controls or in 158 Caucasian literature controls (0/248 total Caucasian controls) (Table II). Thus, in our Caucasian sample this mutation was confined to the two AD+PD patients.

To clarify the genetic relationship between the two ND1$^{3,397[Met \rightarrow Val]}$ AD+PD patients, their mtDNA haplotypes were analyzed. The ADPD1 and ADPD2 mtDNAs differed by seven previously described restriction site variants[55], which placed them on two separate branches of the Caucasian mtDNA phylogeny (FIG. 1). To further substantiate the wide divergence of these two mtDNAs, the entire D-loops from ADPD1 and ADPD2 were sequenced and found to differ by five nucleotide substitutions (nps 16270, 16304, 73, 150, 152) and by a dinucleotide deletion between nps 514 and 523 (FIG. 8). Moreover, the D-loop of the "Cambridge sequence"[57] fell midway between the two patient sequences. Since the Cambridge sequence is known to have an A at np 3,397 while both patients are G, this analysis demonstrates that the ND1$^{3,397[Met \rightarrow Val]}$ mutation must have occurred two independent times (FIG. 8). Since these independent events were associated with the same AD+PD neuropathology, it is possible that this mutation contributes to the pathogenesis of this disease.

Available pedigree information from these two individuals suggests that the ND1$^{3,397[Met \rightarrow Val]}$ mutation may be associated with the maternal transmission of AD. This mutation was present in the blood of the unaffected brother of ADPD2, confirming its maternal inheritance, and a history of cognitive decline was obtained for the mother of ADPD1 and for two maternal aunts of ADPD2.

Extending the population analysis to other ethnic groups showed that the mutation was not found in 63 Africans. However, it was found in 1/207 (0.5%) Asians and in 6/266 (2.3%) American Indians. All six of the American Indian positives were found in a sample of 28 Ticuna, a small, isolated tribe from the upper Amazon. In these six Ticuna, the mutation was found on only two almost identical mtDNA haplotypes which differed by one restriction site and were classified as belonging to the American Indian specific mtDNA haplotype cluster D[54]. Consequently, all six Ticuna represent a single founding mutational event that occurred within this isolated tribe. By contrast, the Asian mutation (an individual from Tibet) occurred on an Asian-specific haplotype[53] which is very different from those observed in the Ticunas (Table II legend). These results indicate that the Ticuna, the Asian, and the two Caucasian mutations are due to four independent mutational events.

In conclusion, the evolutionary conservation of the ND1$^{3,397[Met \rightarrow Val]}$ mutation, its presence in Caucasian patients but not Caucasian controls, and its association with affected maternal relatives suggests that this mutation could contribute to AD+PD pathology. However, the low frequency of the mutation in patients and its occasional appearance in the Asian and American Indian populations also raises the possibility that it is a neutral sequence variant.

The 12S$^{956-965ins}$ Mutation

One patient (ADPD29), within the mtDNA$^{16,304+4,336}$ lineage, was found to harbor a novel 12S rRNA gene insertion (FIG. 1). This insertion increased the size of the encompassing restriction fragment generated by multiple restriction endonucleases (e.g. Alu I, Dde I, Mbo I, etc.) (FIG. 9). Direct sequence analysis revealed that the insertion consisted of approximately five cytosines within the sequence CCCCCTCCCC [SEQ ID NO:3] between nps 956 to 965 (12S$^{956-965ins}$) (FIG. 10). This insertion was not observed in 699 controls including 119 Caucasians[42,58], 241 Asians[53,58], 61 Africans[58], 167 American Indians[54], 90 New Guineans[58,59], or 21 Australian Aboriginese[58], and is the first report of an insertion within a human mtDNA gene. The unique nature of this AD+PD mutation, its absence from the general population, and its association with both the tRNA$^{Gln4,336}$ mutation and the AD+PD phenotype suggest that it may be functionally related to AD+PD.

The Heteroplasmic 16S$^{3,196}$ Mutation

One patient (AD10) (FIG. 1), who lies outside the mtDNA lineage, was found to harbor a heteroplasmic Dde I site loss. This mutation was found in approximately 50% of the mtDNAs of this individual's frontal, temporal, and parietal lobes as well as his basal ganglia and cerebellum. The mutation was sequenced and found to be the result of a G to A transition in the 16S rRNA gene at np 3,196 (16S$^{3,196}$) which also creates an Ssp I site (FIG. 11).

To determine the frequency of this mutation in the general population, 699 individuals were surveyed (see the 16S$^{956-965ins}$ section for references). Two individuals were found to have lost this Dde I site, an American Indian from the Pima tribe[54] and an Asian from Borneo[53]. Direct sequencing revealed that the American Indian was homoplasmic for a C to T transition at np 3,192, while the Asian was homoplasmic for the same np 3,196 mutation as found in AD10 (FIG. 12). Consistent with this result, the Ssp I site was present in the Asian, but absent in the American Indian (FIG. 11). Since the 16S$^{3,196}$ mutation was heteroplasmic in the Alzheimer's disease patient and homoplasmic in the control, the relevance of this mutation to the Alzheimer's disease neuropathology is unclear.

The ND2$^{5460}$ mutations

Recently, it was reported that a high proportion of Alzheimer's disease patients harbored one of two mtDNA mutations in ND2 at np 5460: a G to A transition converting an alanine to threonine and a G to T transversion converting an alanine to serine[60]. To determine the relevance of these mutations to our patients, we employed two restriction endonuclease tests (FIG. 13). The G to A mutation was detected by an Hph I site gain, in which the 332 np PCR fragment was cut into 198 and 134 bp fragments. To test for either the G to A or the G to T mutations at np 5460, we prepared a PCR primer in which the second nucleotide from the 3'-end (np 5458) was changed from a T to C. This created an Aci I site in normal individuals having a G at np 5460, but eliminated the Aci I site when any other nucleotide was substituted at np 5460. In normal individuals, the resulting 208 np PCR product was cut into 190 and 18 np fragments, but in mutants it remained uncut.

The G to A mutation was found in 4.4% (3/68) of patients with AD, AD+PD, and PD. However, it was also present in 8.6% (3/35) of Caucasian controls. Consequently, this mutation does not appear to be specific for Alzheimer's disease or Parkinson's disease and probably is a relatively common polymorphism. The G to T mutation was not detected in any of 67 AD, AD+PD, or PD patients or in 41 controls. Hence, mutations at np 5460 do not appear to play a major role in our AD, AD+PD, or PD patients.

TABLE I

| AD Patients | AD + PD Patients | PD Patients | Total Patients | Caucasian Laboratory Controls | Caucasian Literature Controls | Total Caucasian Controls | Total Laboratory Controls | Total Literature Controls | Total Controls |
|---|---|---|---|---|---|---|---|---|---|
| 3.2% | 6.8% | 5.3% | 5.2% | 0.8% | 0.7% | 0.7% | 0.2% | 0.4% | 0.4% |
| 2/62 | 5/73 | 2/38 | 9/173 | 1/125 | 11/1566 | 12/1691 | 1/547 | 12/2591 | 12/3036 |

Table I.
Association between the tRNA$^{Gln4,336}$ mutation and AD, AD + PD, and PD.
Patients: The AD and AD + PD samples included 62 and 73 Caucasians, respectively. The PD group had 35 Caucasians, 1 Afro-American, and 2 Asians.
Controls: The Laboratory Controls included the following groups. Caucasians of mixed European origin: 125; Africans: 44 (41 Senegalese and 3 Afro-Americans); Asians: 153[53] and 54 Tibetans; American Indians: 167[54]; Unknown ethnic origin: 4.
The Literature Controls included the following groups. Caucasians: a group of 50 Europeans[83], a group of 46 Europeans[58], a group of 46 Europeans (two with the AvaII site gain)[101], 75 Israeli Arabs and Jews (one with the AvaII site gain)[102], 100 Italian Albanians (one with the AvaII site gain)[103], 87 Italian Apulians[104], 90 Italian Sicilians[105], 231 Italians (two with the AvaII site gain)[106], 480 Italians (two with the AvaII site gain)[107], 79 Indian Hindus[108], 110 Finnish (two with the AvaII site gain)[109], 73 British (one AvaII site gain)[110,111], 39 Jews[112], and 60 Italian Calabrians[113]; Africans and Afro-Americans: 74 Bantus and Bushmen[83], 20 Africans and Afro-Americans[58], and 186 Senegalese[113]; Asians: 46 Chinese and Japanese[83], 34 Asians[58], 122 Japanese[115], 116 Japanese[116], 121 Asians[117] and 91 Tharu[118]; American Indians: 30 Warao[83] and 74 Pima and Papagoe[119]; Australian aboriginese and New Guineans: 21 aboriginals[58], 26 Papua New Guineans[58] and 64 Papua New Guineans[59] who were mixed highland and lowland inhabitants. The Total Caucasian Controls included the Literature Controls plus the 125 individuals tested for this study (Laboratory Controls).

TABLE II

| AD Patients | AD + PD Patients | PD Patients | Total Patients | Caucasian Laboratory Controls | Caucasian Literature Controls | Total Caucasian Controls | Total Laboratory Controls | Total Literature Controls | Total Controls |
|---|---|---|---|---|---|---|---|---|---|
| 0% | 2.7% | 0% | 1.2% | 0% | 0% | 0% | *0.3–1.1% | 0% | 0.7% |
| 0/62 | 2/73 | 0/38 | 2/173 | 0/90 | 0/158 | 0/248 | 2–7/612 | 0/439 | 7/1051 |

Table II.
Association between the ND1$^{3,397}$ mutation and AD + PD.
Patients: The AD and AD + PD samples included 62 and 73 Caucasians, respectively. The PD group had 35 Caucasians, 1 Afro-American, and 2 Asians.
Controls: The Laboratory Controls included the following groups. Caucasians: 64 individuals analyzed for this study and 26 previously reported individuals[42]. Asians: 153 Asians[53] and 54 Tibetans. American Indians: 266[54,120]. Africans: 41 Senegalese, 2 Afro-Americans. Unknown ethnic origin: 6. The Literature Controls included the following groups. Caucasians: 46 Europeans[58], 39 Jews[112], 73 British[110,111]. Asians: 34 Asians[58], 116 Japanese[116]. Africans: 20[58]. Australian Aboriginese: 21[58]. Papua New Guineans: 26[58] and 64[59]. The prevalence estimates for the ND1$^{3,397[Met \rightarrow Val]}$ mutation are expressed as a range of values (0.3%–1.1%). The 0.3% estimate represents the number of mutational events, thus lumping the 6 Ticunas Indians together. The 1.1% estimate includes the total number of positive controls, counting all six of the Ticuna as independent events. The two Ticuan and one Tibetan haplotype differ from the Cambridge sequence by the following polymorphisms: Ticuna haplotypes: (A) 3,397+ [RsaI], 4,769– [AluI], 5,176– [AluI], 7,025+ [AluI], 8,858+ [HhaI], 10,394+ [DdeI], 10,397+ [AluI], 13,702– [HaeIII], 14,199– [HincII]. 14,268+ [HinfI], 14,368+ [HinfI], (B) 3,397+ [RsaI], 4,769– [AluI], 5,176– [AluI], 7,025+ [AluI], 8,858+ [HhaI], 10,394+ [DdeI], 10,397+ [AluI], 13,702– [HaeIII], 14,199– [HincII], 14,268+ [HinfI], 14 ,368+ [HinfI], DdeI– [15,073]. Asian haplotype: 663+ [HaeIII], 3,397+ [RsaI], 4,769– [AluI], 7,025+ [AluI], 8,858+ [HhaI], 13,702– [HaeIII], 14,199– [HincII], 14,268+ [HinfI], 14,368+ [HinfI].
(+) = site gain and (–) = site loss relative to the published sequence 57.

TABLE III

|  |  | Patients | Controls |
|---|---|---|---|
| ND2$^{5460}$ | G → A | 3/68 (4.4%) | 3/35 (8.6%) |
| ND2$^{5460}$ | G → T | 0/67 (0%) | 0/41 (0%) |

Table III:
Distribution of the ND2$^{5460}$ polymorphism in individuals with AD, AD + PD, and AD and controls.

REFERENCES

1. Whitehouse, P. J. et al. Science 215, 1237–1239 (1982).
2. Chui, H. C., Teng, E. L., Henderson, V. W. & Moy, A. C. Neurology 35, 1544–1550 (1985).
3. Mayeux, R., Stern, Y. & Spanton, S. Neurology. 35, 453–461 (1985).
4. Ditter, S. M. & Mirra, S. S. Neurology. 37, 754–760 (1987).
5. Mirra, S. S. et al. Neurology 41, 479–86 (1991).
6. Hansen, L. A. et al. Neurology 40, 1–8 (1990).
7. Byrne, E. J., Lennox, G., Lowe, J. & Godwin-Austin, R. J. Neurol. Neurosurg. Psychiatry. 52, 709–717 (1989).
8. Perry, R. H., Irving, D., Blessed, G., Fairbairn, A. & Perry, E. K. J. Neurol. Sci. 95, 119–139 (1990).
9. Dickson, D. W. et al. Acta Neuropathol. 78, 572–84 (1989).
10. Crain, B. J. & Mirra, S. S. Current Opinion Neurol. Neurosurg. 921–925 (1990).
11. Wallace, D. C. Science 256, 628–632 (1992).
12. Wallace, D. C. Ann. Rev. Biochem. 61, 1175–1212 (1992).
13. Mizuno, Y. et al. Blochem. Biophys. Res. Commun. 163, 1450–1455 (1989).
14. Schapira, A. H. V. et al. Lancet 1,1269 (1989).
15. Schapira, A. H. V. et al. J. Neurochem. 54, 823–827 (1990).
16. Parker, W. D., Boyson, S. J. & Parks, J. K. Ann. Neurol. 26, 719–723 (1989).
17. Bindoff, L. A., Birch-Machin, M. A., Cartlidge, N. E. F., Parker, Jr., W. D. & Turnbull, D. M. J. Neurol. Sci. 104, 203–208 (1991).
18. Shoffner, J. M., Watts, R. L., Juncos, J. L., Torroni, A. & Wallace, D. C. Ann. Neurol. 30, 332–339 (1991).
19. Parker, W. D., Filley, C. M. & Parks, J. K. Neurology 40, 1302–1303 (1990).
20. Sims, N. R., Finegan, J. M., Blass, J. P., Bowen, D. M. & Neary, D. Brain Res. 436, 30–38 (1987).
21. Peterson, C & Goldman, J. E. Proc. Natl. Acad. Sci. USA 83, 2758–2762 (1986).

22. Blass, J. P., Baker, A. C., Ko, L. & Black, R. S. Arch. Neurol. 47, 864–869 (1990).
23. Shoffner, J. M. & Wallace, D. C. Adv. Hum. Genet. 19, 267–330 (1990).
24. Hansen, L. A., Masliah, E., Terry, R. D. & Mirra, S. S. Acta Neuropathol. 78, 194–201 (1989).
25. Saraiva, A. A., Borges, M. M., Madeira, M. D., Tavares, M. A. & Paula-Barbosa, M. M. J. Submicrosc. Cytol. 17, 459–64 (1985).
26. Giles, R. E., Blanc, H., Cann, H. M. & Wallace, D. C. Proc. Natl. Acad. Sci. USA 77, 6715–6719 (1980).
27. Case, J. T. & Wallace, D. C. Somat. Cell Genet. 7, 103–108 (1981).
28. Wallace, D. C. Somat. Cell Mol. Genet. 12, 41–49 (1986).
29. Lott, M. T., Voljavec, A. S. & Wallace, D. C. Am. J. Ophthalmol. 109, 625–631 (1990).
30. Shoffner, J. M. et al. Proc. Natl. Acad. Sci. USA 86, 7952–7956 (1989).
31. Shoffner, J. M. et al. Cell 61, 931–937 (1990).
32. Wallace, D. C. et al. Cell 55, 601–610 (1988).
33. Holt, I. J., Harding, A. E., Petty, R. K. H. & Morgan-Hughes, J. A. Am. J. Hum. Genet. 46, 428–433 (1990).
34. Trounce, I., Byrne, E. & Marzuki, S. Lancet 1, 637–639 (1989).
35. Yen, T. -C., Chen, Y. -S., King, K. -L., Yeh, S. -H. & Wei, Y. -H. Biochem. Biophys. Res. Commun. 165, 994–1003 (1989).
36. Muller-Hocker, J. Am. J. Pathol. 134, 1167–1173 (1989).
37. Cortopassi, G. A. & Arnheim, N. Nucleic Acids Res. 18, 6927–6933 (1990).
38. Corral-Debrinski, M. et al. J. A. M. A. 266, 1812–1816 (1991).
39. Ikebe, S. et al. Biochem. Biophys. Res. Commun. 170, 1044–1048 (1990).
40. Ozawa, T. et al. Biochem. Biophys. Res. Commun. 170, 830–836 (1990).
41. Wallace, D. C. et al. Science 242, 1427–1430 (1988).
42. Brown, M. D. et al. Genetics 130, 163–173 (1992).
43. Newman, N. J. & Wallace, D. C. Am. J. Ophthal. 109, 727–730 (1990).
44. Brown, M. D., Voljavec, A. S., Lott, M. T., MacDonald, I. & Wallace, D. C. FASEB Journal 6,2791–2799 (1992).
45. Johns, D. R. & Berman, J. Biochem. Biophys. Res. Commun. 174, 1324–1330 (1991).
46. Johns, D. R. & Neufeld, M. J. Biochem. Biophys. Res. Commun. 181, 1358–1364 (1991).
47. Vilkki, J., Ott, J., Savontaus, M. L., Aula, P. & Nikoskelainen, E. K. Am. J. Hum. Genet. 48, 486–491 (1991).
48. Howell, N., Kubacka, I., Yu, M. & McCullough, D. A. Am. J. Hum. Genet. 48, 935–942 (1991).
49. Howell, N. et al. Am. J. Hum. Genet. 49, 939–950 (1991).
50. Huoponen, K., Vilkki, J., Aula, P., Nikoskelainen, E. K. & Savontaus, M. L. Am. J. Hum. Genet. 48, 1147–1153 (1991).
51. Brown, M. D. et al. Am. J. Hum. Genet. 51,378–385 (1992).
52. Singh, G., Lott, M. T. & Wallace, D. C. N. Engl. J. Med. 320, 1300–1305 (1989).
53. Ballinger, S. W. et al. Genetics 130, 139–152 (1992).
54. Torroni, A. et al. Genetics 130, 153–162 (1992).
55. Wallace, D. C., Lott, M. T., Torroni, A. & Shoffner, J. M. Cytogenet. Cell Genetic. 58, 1103–1123 (1991).
56. Burger, G. & Werner, S. J. Mol. Biol. 186, 231–242 (1985).
57. Anderson, S. et al. Nature 290, 457–465 (1981).
58. Cann, R. L., Stoneking, M. & Wilson, A. C. Nature 325, 31–36 (1987).
59. Stoneking, M., Jordem, L. B., Bhatia, K. & Wilson, A. C. Genetics. 124, 717–733 (1990).
60. Lin, F. -H. et al. Biochem. Biophys. Res. Commun. 182, 238–246 (1992).
61. Farrer, L. A., Myers, R. H., Connor, L., Cupples, L. A. & Growdon J. H. Am. J. Hum. Genet. 48, 1026–1033 (1991).
62. Haines, J. Am. J. Hum. Genet. 48, 1021–1025 (1991).
63. Pericak-Vance, M. A. et al. Am. J. Hum. Genet. 48, 1034–1050 (1991).
64. Chartier-Harlin, M. C. et al. Nature 353, 844–846 (1991).
65. Goate, A. et al. Nature 349, 704–706 (1991).
66. Murrell, J., Farlow, M., Ghetti, B. & Benson, M. D. Science 254, 97–99 (1991).
67. Naruse, S. et al. Lancet 337, 978–979 (1991).
68. Yoshioka, K., Miki, T., Katsuya, T., Ogihara, T. & Sakaki, Y. Biochem. Biophys. Res. Commun. 178, 1141–1146 (1991).
69. Tanzi, R. E. et al. Nature 329,156–157 (1987).
70. Van Broeckhoven, C. et al. Nature 329, 153–155 (1987).
71. Johnson, W. G. Neurology 41,82–87 (1991).
72. Golbe, L. I. Neurology 40, 7–14 (1990).
73. Goto, Y, -i., Tojo, M., Tohyama, J., Horai, S., & Nonaka, I. Ann. Neurol. 31,672–675 (1992).
74. Goto, Y., Nonaka, I. & Horai, S. Nature 348, 651–653 (1990).
75. Kobayashi, Y. et al. Blochem. Biophys. Res. Commun. 173, 816–822 (1990).
76. Kosik, K. S. Science 256,780–783 (1992).
78. Zeviani et al., Lancet 338,143–147 (1991).
79. Singer, T. P. & Ramsey, R. R. FEBS Lett. 274, 1–8 (1990).
80. Beal, M. F. Ann. Neurol. 31, 119–130 (1992).
81. Khachaturian, Z. S. Arch. Neurol. 42, 1097–1105 (1985).
82. Wilkinson L. SYSTAT: The System for Statistics. Evanston, Ill.: SYSTAT, Inc 1989:142–179,462–463.
83. Johnson, M. J., Wallace, D. C., Ferris, S. D., Rattazi, M. C. & Cavalli-Sforza, L. L. J. Mol. Evol. 19, 255–271 (1983).
84. Cann, R. L., Brown, W. M. & Wilson, A. C. Genetics 106, 479–499 (1984).
85. Swofford, D. L. PAUP: Phylogenetic analysis using parsimony, version 3.0. Computer program distributed by the Illinois Natural History Survey, Champaign, Ill. (1990).
86. Nei, M. & Tajima, F. Genetics 105, 207–217 (1983).
87. Vigilant, L., Pennington, R., Harpending, H., Kocher, T. D. & Wilson, A. C. Proc. Natl. Acad. Sci. USA 86, 9350–9354 (1989).
88. Anderson, S. et al. J. Mol. Biol. 156, 683–717 (1982).
89. Bibb, M. J., Van Etten, R. A., Wright, C. T., Walberg, M. W. & Clayton, D. A. Cell 26, 167–180 (1981).
90. Gadaleta, G. et al. J. Mol. Evol. 28, 497–516 (1989).
91. Desjardins, P. & Morals, R. J. Mol. Biol. 212, 599–634 (1990).
92. Roe, B. A., Ma, D. -P., Wilson, R. K. & Wong, J. F. -H. J. Biol. Chem. 17, 9759–9774 (1985).
93. Jacobs, H. T., Elliott, D. J., Veerabhadracharya, B. M. & Farquharson, A. J. Mol. Biol. 202, 185–217 (1988).
94. Clary, D. O. & Wolstenholme, D. R. J. Mol. Evol. 22, 252–271 (1985).
95. Okimoto, R., Macfarlane, J. L., Clary, D. O. & Wolstenholme, D. R. Genetics 130, 471–498 (1992).
96. Pritchard, A. E., Sable, C. L., Venuti, S. E. & Cummings, D. J. Nucleic Acids Res. 18, 163–171 (1990).

97. Cummings, D. J., Domenico, J. M., & Michel, F. Curr. Genet. 14, 253–264 (1988).
98. Boer, P. H. & Gray, M. W. EMBO J. 7,3501–3508 (1988).
99. Zwieb, C., Glotz, C. & Brimacombe, R. Nucleic Acids Res. 9, 3621–3640 (1981).
101. Dionne et al., Med. Sci. Sports Exerc. 23, 177–185 (1991).
100. Glotz, C., Zwieb, C. & Brimacombe, R. Nucleic Acids Res. 9, 3287–3306 (1981).
102. Bonne-Tamir, B., Johnson, M. J., Natali, A., Wallace, D. C. & Cavalli Sforza, L. L. Am. J. Hum. Genet. 38, 341–351 (1986).
103. Torroni, A. et al. Int. J. Anthropol. 5, 97–104 (1990).
104. De Benedictis, G., Rose, G., Passarino, G. & Quagliariello, C. Ann. Hum. Genet. 53, 311–318 (1989).
105. Semino, O. et al. Ann. Hum. Genet. 53, 193–202 (1989).
106. Brega, A. et al. Ann Hum. Genet. 50, 327–338 (1986).
107. Sartoris, S. et al. Ann. Hum. Genet. 52, 327–340 (1988).
108. Semino, O., Torroni, A., Scozzari, R., Brega, A. & Santachiara Benerecetti, A. S. Ann. Hum. Genet. 55, 123–136 (1991).
109. Vilkki, J., Savontaus, M. L. & Nikoskelainen, E. K. Hum. Genet. 80, 317–321 (1988).
110. Holt, I. J., Harding, A. E. & Morgan-Hughes, J. A. Hum. Genet. 79, 53–57 (1988).
111. Holt, I. J., Miller, D. H. & Harding, A. E. J. Neurol. Neurosurg. Psychiatry 51,1075–1077 (1988).
112. Tikochinski, Y., Ritte, U., Gross, S. R., Prager, E. M. & Wilson, A. C. Am. J. Hum. Genet. 48, 129–136 (1991).
113. De Benedictis, G., Rose, G., Caccio, S., Picardi, P., & Quagliariello, C. Gene. Geogr. 3, 33–40 (1989).
114. Scozzari, R. et al. Am. J. Hum. Genet. 43, 534–544 (1988).
115. Harihara, S., Hirai, M. & Omoto, K. Japanese J. Hum. Genet. [Jinrui Idengaku Zasshi] 31, 73–83 (1986).
116. Horai, S. & Matsunaga, E. Hum. Genet. 72, 105–117 (1986).
117. Harihara, S. et al. Am. J. Hum. Genet. 43, 134–143 (1988).
118. Brega, A. et at. Am. J. Hum. Genet. 39, 502–512 (1986).
119. Wallace, D. C., Garrison, K. & Knowler, W. C. Am. J. Phys. Anthropol. 68, 149–155 (1985).
120. Schurr, T. G. et al. Am. J. Hum. Genet. 46, 613–623 (1990).
121. Majander, A., Huoporien, K., Savontaus, M. -L., Nikoskelainen, E., & Wikstrom, M. FEBS Letters 292, 289–292 (1991).
122. Larsson, N. -G. et al. Am. J. Hum. Genet. 50,360–363 (1992).
123. Parker, W. D., Oley, C. A., & Parks, J. K. Lancet 320,1331–1333 (1989).
124. Maniatis et al. (1989) Molecular Cloning: A Laboratory Manual, 2nd Ed., Cold Spring Harbor Laboratory, Cold Spring Harbor, N.Y.
125. Berger and Kimmel (1987) "Guide to Molecular Cloning Techniques," Methods in Enzymology, Volume 152, Academic Press, Inc., San Diego, Calif.
126. Gibbs et al. (1989) Nucleic Acids Res. 17:2437.
127. Kwok et al. (1990) Nucleic Acids Res. 18:999.
128. Miyada et al. (1987) Methods Enzymol. 154:94.
129. Anderson et al., Nature 290:457–465 (1981).
130. Dihella et al. (1988) Lancet 1:497.
131. Promega Protocols and Applications Guide (1991) Promega Corporation, Madison, Wis.
132. Orita et al. (1989) Genomics 5:874–879.
133. Orita et al. (1990) Genomics 6:271–276.
134. Newton et al. (1989) Nucleic Acids Res. 17:2503.
135. Nichols et al. (1989) Genomics 5:535.
136. Okayama et al. (1989) J. Lab. Clin. Med. 114:105.
137. Sarkar et al. (1990) Anal. Blochem. 186:64.
138. Sommer et al. (1989) Mayo Clin. Proc. 64:1361.
139. Wu (1989) Proc. Natl. Acad. Sci. (U.S.A.) 86:2757
140. Dutton et al. (1991) Biotechniques 11:700.
150. Baany et al. (1991) Proc. Natl. Acad. Sci. (U.S.A.) 88:189.
151. R. A. Weiss (1991) Science 254:1992.
152. Frohman and Martin, Cell (1989) 56:145.
153. Wirak et al., the EMBO Journal, 10(2) 289–296 (1991).
154. Schilling et al., Gene 98(2) 225–230 (1991).
155. Quon, et al. (1991) Nature 352:239.
156. Wirak, et al. (1991) Science 253:323.
157. Kawabata, et al. (1991) Nature 354:476.
158. Mendelson et al. Virology 166:154–165.
159. Wondisford et al. (1988) Molec. Endocrinol. 2:32–39 (1988).
160. Kohler and Milstein, (1975) Nature 256:495–497.
161. Antibodies: A Laboratory Manual, Harlow and Lane (1988), Cold Spring Harbor Laboratory, Cold Spring Harbor, N.Y.
162. Winacker (1987) "From Genes to Clones," VCH Publishers, New York, N.Y.).
163. Quenn et al. (1986) Immunol. Rev. 89:49–68.

What is claimed is:

1. A method of detecting subjects at increased risk for mitochondrial-associated Alzheimer's disease and/or Parkinson's disease, comprising:

obtaining a sample comprising nucleic acids from the subjects; and detecting in the nucleic acids the presence of a mutation of mitochondrial DNA which correlates to Alzheimer's disease and/or Parkinson's disease, thus identifying subjects at increased risk for these diseases, wherein the mutation is in nucleotide position 4,336 of mitochondrial DNA.

2. The method of claim 1, wherein the detecting step comprises combining a nucleotide probe which selectively hybridizes to a nucleic acid containing the mutation with the nucleic acids in the sample and detecting the presence of hybridization.

3. The method of claim 1, wherein the detecting step comprises amplifying a nucleic acid product comprising the nucleotide of the mutation and detecting the presence of the mutation in the amplified product.

4. The method of claim 1, wherein the detecting step comprises selectively amplifying a nucleic acid product comprising the nucleotide of the mutation and detecting the presence of amplification.

5. The method of claim 1, wherein the detecting step comprises detecting the gain or loss of a restriction endonuclease site as detected by enzyme digest of a nucleic acid comprising the nucleotide of the mutation.

6. The method of claim 1, wherein the detecting step comprises utilizing the Ligase Chain Reaction, wherein the nucleic acids are allowed to hybridize both with oligonucleotides which are fully complementary to a portion of the nucleic acids containing the nucleotide of the mutation, and oligonucleotides having a mismatch with respect to the nucleotide, under conditions which will distinguish between the two.

7. A method of detecting subjects at increased risk for mitochondrial-associated Alzheimer's disease and/or Parkinson's disease, comprising:

obtaining a sample comprising nucleic acids from the subjects; and detecting in the nucleic acids the presence of a mutation of mitochondrial DNA which correlates to Alzheimer's disease and/or Parkinson's disease, thus identifying subjects at increased risk for these diseases, wherein the mutation is in nucleotide position 3,397 of mitochondrial DNA.

8. The method of claim 7, wherein the detecting step comprises combining a nucleotide probe capable of selectively hybridizing to a nucleic acid containing the mutation with a nucleic acid in the sample and detecting the presence of hybridization.

9. The method of claim 7, wherein the detecting step comprises amplifying a nucleic acid product comprising the nucleotide of the mutation and detecting the presence of the mutation in the amplified product.

10. The method of claim 7, wherein the detecting step comprises selectively amplifying a nucleic acid product comprising the nucleotide of the mutation and detecting the presence of the product.

11. The method of claim 7, wherein the detecting step comprises detecting the gain or loss of a restriction endonuclease site as detected by enzyme digest of a nucleic acid comprising the nucleotide of the mutation.

12. The method of claim 7, wherein the detecting step comprises utilizing Ligase Chain Reaction, wherein the nucleic acids are allowed to hybridize both with oligonucleotides which are fully complementary to a portion of the nucleic acids containing the nucleotide of the mutation, and oligonucleotides having a mismatch with respect to the nucleotide, under conditions which will distinguish between the two.

* * * * *